United States Patent
Hall et al.

(10) Patent No.: US 10,190,121 B2
(45) Date of Patent: Jan. 29, 2019

(54) APTAMERS AGAINST EGFR AND THERAPEUTIC USES THEREOF

(71) Applicant: Altermune Limited, London (GB)

(72) Inventors: Bradley Hall, London (GB); Paul Hatala, London (GB)

(73) Assignee: Avvinity Therapeutics Limited, Waterbeach, Cambridge (GB)

( * ) Notice: Subject to any disclaimer, the term of this patent is extended or adjusted under 35 U.S.C. 154(b) by 0 days.

(21) Appl. No.: 15/320,929

(22) PCT Filed: Jun. 23, 2015

(86) PCT No.: PCT/GB2015/051812
§ 371 (c)(1),
(2) Date: Dec. 21, 2016

(87) PCT Pub. No.: WO2015/198024
PCT Pub. Date: Dec. 30, 2015

(65) Prior Publication Data
US 2017/0130226 A1 May 11, 2017

(30) Foreign Application Priority Data
Jun. 23, 2014 (GB) .................................. 1411150.4

(51) Int. Cl.
*C12N 15/115* (2010.01)
(52) U.S. Cl.
CPC ........ *C12N 15/115* (2013.01); *C12N 2310/16* (2013.01); *C12N 2310/317* (2013.01); *C12N 2310/321* (2013.01); *C12N 2310/322* (2013.01); *C12N 2310/344* (2013.01); *C12N 2310/351* (2013.01); *C12N 2310/3513* (2013.01); *C12N 2320/51* (2013.01)
(58) Field of Classification Search
CPC .............. C12N 15/115; C12N 2310/16; C12N 2310/317; C12N 2310/321; C12N 2310/322
See application file for complete search history.

(56) References Cited

U.S. PATENT DOCUMENTS

| 2011/0287956 A1* | 11/2011 | Iqbal | .................. G01N 33/5308 |
| | | | 506/9 |
| 2015/0190529 A1* | 7/2015 | Peterson | .......... A61K 47/48569 |
| | | | 424/178.1 |

FOREIGN PATENT DOCUMENTS

| WO | 01/74382 A1 | 10/2001 |
| WO | 2005/079423 A2 | 9/2005 |
| WO | 2006/088888 A2 | 8/2006 |
| WO | 2010/129666 A1 | 11/2010 |
| WO | 2012/049112 A1 | 4/2012 |
| WO | 2014/067551 A1 | 5/2014 |

OTHER PUBLICATIONS

Viswatej Avutu: "Avidity Effects of MinE07, an Anti-EGFR Aptamer, on Binding to A431 Cells", Sep. 6, 2011 (Sep. 6, 2011), pp. 1-28, XP055210258, Retrieved from the Internet: URL:http://repositories.lib.utexas.edu/bitstream/handle/2152/13407/Avutu-Bioch_10.pdf?sequence=2 [retrieved on Aug. 31, 2015].
Na Li et al: "Inhibition of Cell Proliferation by an Anti-EGFR Aptamer", PLOS One, vol. 6, No. 6, Jun. 8, 200 (Jun. 8, 2011), p. e20299, XP055210163, DOI: 10.1371/journal.pone.0020299.
Gwendolyn M. Stovall et al: "In Vitro Selection Using Modified or Unnatural Nucleotides" In: "Current Protocols in Nucleic Acid Chemistry", Mar. 26, 2014 (Mar. 26, 2014), John Wiley & Sons, Inc., Hoboken, NJ, USA, XP055210370, ISBN: 978-0-47-114270-6 pp. 9.6.1-9.6.33, DOI: 10.1002/0471142700.nc0906s56, the whole document.

* cited by examiner

*Primary Examiner* — Brian A Whiteman
(74) *Attorney, Agent, or Firm* — Hahn Loeser & Parks, LLP

(57) ABSTRACT

The invention relates to novel aptamers, in particular aptamers which are capable of binding to EGFR. The invention also relates to cancer cell binding complexes comprising said aptamers and the use of said cancer cell binding complexes in the treatment of cancer.

14 Claims, 16 Drawing Sheets

Specification includes a Sequence Listing.

SEQUENCE LISTING

```
<160> NUMBER OF SEQ ID NOS: 85

<210> SEQ ID NO 1
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: misc_feature
<222> LOCATION: (1)..(2)
<223> OTHER INFORMATION: absent or G
<220> FEATURE:
<221> NAME/KEY: misc_feature
<222> LOCATION: (3)..(3)
<223> OTHER INFORMATION: absent or A
<220> FEATURE:
<221> NAME/KEY: misc_feature
<222> LOCATION: (4)..(4)
<223> OTHER INFORMATION: absent or C
```

```
<220> FEATURE:
<221> NAME/KEY: misc_feature
<222> LOCATION: (5)..(6)
<223> OTHER INFORMATION: absent or G
<220> FEATURE:
<221> NAME/KEY: misc_feature
<222> LOCATION: (7)..(7)
<223> OTHER INFORMATION: absent or A
<220> FEATURE:
<221> NAME/KEY: misc_feature
<222> LOCATION: (8)..(9)
<223> OTHER INFORMATION: absent or U
<220> FEATURE:
<221> NAME/KEY: misc_feature
<222> LOCATION: (45)..(45)
<223> OTHER INFORMATION: absent or G
<220> FEATURE:
<221> NAME/KEY: misc_feature
<222> LOCATION: (46)..(46)
<223> OTHER INFORMATION: absent or U
<220> FEATURE:
<221> NAME/KEY: misc_feature
<222> LOCATION: (47)..(47)
<223> OTHER INFORMATION: absent or C

<400> SEQUENCE: 1
nnnnnnnnnu aaucgccgua gaaaagcaug ucaaagccgg aaccnnnc           48

<210> SEQ ID NO 2
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: misc_feature
<222> LOCATION: (1)..(2)
<223> OTHER INFORMATION: absent or G
<220> FEATURE:
<221> NAME/KEY: misc_feature
<222> LOCATION: (3)..(3)
<223> OTHER INFORMATION: absent or A
<220> FEATURE:
<221> NAME/KEY: misc_feature
<222> LOCATION: (4)..(4)
<223> OTHER INFORMATION: absent or 2'-fluoro-C
<220> FEATURE:
<221> NAME/KEY: misc_feature
<222> LOCATION: (5)..(6)
<223> OTHER INFORMATION: absent or G
<220> FEATURE:
<221> NAME/KEY: misc_feature
<222> LOCATION: (7)..(7)
<223> OTHER INFORMATION: absent or A
<220> FEATURE:
<221> NAME/KEY: misc_feature
<222> LOCATION: (8)..(9)
<223> OTHER INFORMATION: absent or 2'-fluoro-U
<220> FEATURE:
<221> NAME/KEY: modified_base
<222> LOCATION: (10)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
```

```
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: misc_feature
<222> LOCATION: (45)..(45)
<223> OTHER INFORMATION: absent or G
<220> FEATURE:
<221> NAME/KEY: misc_feature
<222> LOCATION: (46)..(46)
<223> OTHER INFORMATION: absent or 2'-fluoro-U
<220> FEATURE:
<221> NAME/KEY: misc_feature
<222> LOCATION: (47)..(47)
<223> OTHER INFORMATION: absent or 2'-fluoro-C
<220> FEATURE:
<221> NAME/KEY: modified_base
<222> LOCATION: (48)..(48)
<223> OTHER INFORMATION: modified 2'-fluoro nucleotide

<400> SEQUENCE: 2
nnnnnnnnnu aaucgccgua gaaaagcaug ucaaagccgg aaccnnnc            48

<210> SEQ ID NO 3
<211> LENGTH: 45
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: modified 2'-fluoro nucleotide
<220> FEATURE:
<221> NAME/KEY: modified_base
<222> LOCATION: (5)..(7)
<223> OTHER INFORMATION: modified 2'-fluoro nucleotide
<220> FEATURE:
<221> NAME/KEY: modified_base
<222> LOCATION: (10)..(11)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(16)
<223> OTHER INFORMATION: modified 2'-fluoro nucleotide
<220> FEATURE:
<221> NAME/KEY: modified_base
<222> LOCATION: (24)..(24)
<223> OTHER INFORMATION: modified 2'-fluoro nucleotide
<220> FEATURE:
<221> NAME/KEY: modified_base
<222> LOCATION: (26)..(26)
<223> OTHER INFORMATION: modified 2'-fluoro nucleotide
<220> FEATURE:
<221> NAME/KEY: modified_base
<222> LOCATION: (28)..(29)
<223> OTHER INFORMATION: modified 2'-fluoro nucleotide
<220> FEATURE:
<221> NAME/KEY: modified_base
```

```
<222> LOCATION: (34)..(35)
<223> OTHER INFORMATION: modified 2'-fluoro nucleotide
<220> FEATURE:
<221> NAME/KEY: modified_base
<222> LOCATION: (40)..(41)
<223> OTHER INFORMATION: modified 2'-fluoro nucleotide
<220> FEATURE:
<221> NAME/KEY: modified_base
<222> LOCATION: (43)..(45)
<223> OTHER INFORMATION: modified 2'-fluoro nucleotide

<400> SEQUENCE: 3
cggauuuaau cgccguagaa aagcauguca aagccggaac cgucc              45

<210> SEQ ID NO 4
<211> LENGTH: 45
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (5)..(7)
<223> OTHER INFORMATION: modified 2'-fluoro nucleotide
<220> FEATURE:
<221> NAME/KEY: modified_base
<222> LOCATION: (10)..(11)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(16)
<223> OTHER INFORMATION: modified 2'-fluoro nucleotide
<220> FEATURE:
<221> NAME/KEY: modified_base
<222> LOCATION: (24)..(24)
<223> OTHER INFORMATION: modified 2'-fluoro nucleotide
<220> FEATURE:
<221> NAME/KEY: modified_base
<222> LOCATION: (26)..(26)
<223> OTHER INFORMATION: modified 2'-fluoro nucleotide
<220> FEATURE:
<221> NAME/KEY: modified_base
<222> LOCATION: (28)..(29)
<223> OTHER INFORMATION: modified 2'-fluoro nucleotide
<220> FEATURE:
<221> NAME/KEY: modified_base
<222> LOCATION: (34)..(35)
<223> OTHER INFORMATION: modified 2'-fluoro nucleotide
<220> FEATURE:
<221> NAME/KEY: modified_base
<222> LOCATION: (40)..(41)
<223> OTHER INFORMATION: modified 2'-fluoro nucleotide
<220> FEATURE:
<221> NAME/KEY: modified_base
<222> LOCATION: (43)..(45)
<223> OTHER INFORMATION: modified 2'-fluoro nucleotide

<400> SEQUENCE: 4
ggaauuuaau cgccguagaa aagcauguca aagccggaac cgucc              45

<210> SEQ ID NO 5
<211> LENGTH: 42
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (2)..(4)
<223> OTHER INFORMATION: modified 2'-fluoro nucleotide
<220> FEATURE:
```

```
<221> NAME/KEY: modified_base
<222> LOCATION: (7)..(8)
<223> OTHER INFORMATION: modified 2'-fluoro nucleotide
<220> FEATURE:
<221> NAME/KEY: modified_base
<222> LOCATION: (10)..(11)
<223> OTHER INFORMATION: modified 2'-fluoro nucleotide
<220> FEATURE:
<221> NAME/KEY: modified_base
<222> LOCATION: (13)..(13)
<223> OTHER INFORMATION: modified 2'-fluoro nucleotide
<220> FEATURE:
<221> NAME/KEY: modified_base
<222> LOCATION: (21)..(21)
<223> OTHER INFORMATION: modified 2'-fluoro nucleotide
<220> FEATURE:
<221> NAME/KEY: modified_base
<222> LOCATION: (23)..(23)
<223> OTHER INFORMATION: modified 2'-fluoro nucleotide
<220> FEATURE:
<221> NAME/KEY: modified_base
<222> LOCATION: (25)..(26)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (40)..(42)
<223> OTHER INFORMATION: modified 2'-fluoro nucleotide

<400> SEQUENCE: 5
auuuaaucgc cguagaaaag caugucaaag ccggaaccgu cc                          42

<210> SEQ ID NO 6
<211> LENGTH: 42
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (5)..(7)
<223> OTHER INFORMATION: modified 2'-fluoro nucleotide
<220> FEATURE:
<221> NAME/KEY: modified_base
<222> LOCATION: (10)..(11)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(16)
<223> OTHER INFORMATION: modified 2'-fluoro nucleotide
<220> FEATURE:
<221> NAME/KEY: modified_base
<222> LOCATION: (24)..(24)
<223> OTHER INFORMATION: modified 2'-fluoro nucleotide
<220> FEATURE:
<221> NAME/KEY: modified_base
<222> LOCATION: (26)..(26)
<223> OTHER INFORMATION: modified 2'-fluoro nucleotide
<220> FEATURE:
<221> NAME/KEY: modified_base
<222> LOCATION: (28)..(29)
<223> OTHER INFORMATION: modified 2'-fluoro nucleotide
<220> FEATURE:
<221> NAME/KEY: modified_base
<222> LOCATION: (34)..(35)
<223> OTHER INFORMATION: modified 2'-fluoro nucleotide
```

```
<220> FEATURE:
<221> NAME/KEY: modified_base
<222> LOCATION: (40)..(42)
<223> OTHER INFORMATION: modified 2'-fluoro nucleotide

<400> SEQUENCE: 6
gggauuuaau cgccguagaa aagcauguca aagccggaac cc                        42

<210> SEQ ID NO 7
<211> LENGTH: 39
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: modified 2'-fluoro nucleotide
<220> FEATURE:
<221> NAME/KEY: modified_base
<222> LOCATION: (4)..(5)
<223> OTHER INFORMATION: modified 2'-fluoro nucleotide
<220> FEATURE:
<221> NAME/KEY: modified_base
<222> LOCATION: (7)..(8)
<223> OTHER INFORMATION: modified 2'-fluoro nucleotide
<220> FEATURE:
<221> NAME/KEY: modified_base
<222> LOCATION: (10)..(10)
<223> OTHER INFORMATION: modified 2'-fluoro nucleotide
<220> FEATURE:
<221> NAME/KEY: modified_base
<222> LOCATION: (18)..(18)
<223> OTHER INFORMATION: modified 2'-fluoro nucleotide
<220> FEATURE:
<221> NAME/KEY: modified_base
<222> LOCATION: (20)..(20)
<223> OTHER INFORMATION: modified 2'-fluoro nucleotide
<220> FEATURE:
<221> NAME/KEY: modified_base
<222> LOCATION: (22)..(23)
<223> OTHER INFORMATION: modified 2'-fluoro nucleotide
<220> FEATURE:
<221> NAME/KEY: modified_base
<222> LOCATION: (28)..(29)
<223> OTHER INFORMATION: modified 2'-fluoro nucleotide
<220> FEATURE:
<221> NAME/KEY: modified_base
<222> LOCATION: (34)..(35)
<223> OTHER INFORMATION: modified 2'-fluoro nucleotide
<220> FEATURE:
<221> NAME/KEY: modified_base
<222> LOCATION: (36)..(36)
<223> OTHER INFORMATION: natural 2'-OH (RNA) nucleotide
<220> FEATURE:
<221> NAME/KEY: modified_base
<222> LOCATION: (37)..(39)
<223> OTHER INFORMATION: modified 2'-fluoro nucleotide

<400> SEQUENCE: 7
uaaucgccgu agaaaagcau gucaaagccg gaaccgucc                            39

<210> SEQ ID NO 8
<211> LENGTH: 48
<212> TYPE: RNA
<213> ORGANISM: Artificial
<220> FEATURE:
<223> OTHER INFORMATION: Synthetic aptamer

<400> SEQUENCE: 8
ggacggauuu aaucgccgua gaaaagcaug ucaaagccgg aaccgucc                  48

<210> SEQ ID NO 9
```

```
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 9
ggacggauuu aaucgccgua gaaaagcaug ucaaagccgg aaccgucc                48

<210> SEQ ID NO 10
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-OMe substituted nucleotide
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
```

-continued

```
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (45)..(45)
<223> OTHER INFORMATION: natural 2'-OH (RNA) nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 10
ggacggauuu aaucgccgua gaaaagcaug ucaaagccgg aaccgucc           48

<210> SEQ ID NO 11
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (2)..(2)
<223> OTHER INFORMATION: 2'-OMe substituted nucleotide
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
```

```
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 11
ggacggauuu aaucgccgua gaaaagcaug ucaaagccgg aaccgucc            48

<210> SEQ ID NO 12
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (3)..(3)
<223> OTHER INFORMATION: 2'-OMe substituted nucleotide
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (45)..(45)
<223> OTHER INFORMATION: natural 2'-OH (RNA) nucleotide
<220> FEATURE:
<221> NAME/KEY: modified_base
<222> LOCATION: (46)..(48)
<223> OTHER INFORMATION: modified 2'-fluoro nucleotide
```

-continued

<400> SEQUENCE: 12
ggacggauuu aaucgccgua gaaaagcaug ucaaagccgg aaccgucc                48

<210> SEQ ID NO 13
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: 2'-OMe substituted nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 13
ggacggauuu aaucgccgua gaaaagcaug ucaaagccgg aaccgucc                48

<210> SEQ ID NO 14
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (5)..(5)
<223> OTHER INFORMATION: 2'-OMe substituted nucleotide
<220> FEATURE:
<221> NAME/KEY: modified_base
<222> LOCATION: (8)..(10)

```
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 14
ggacggauuu aaucgccgua gaaaagcaug ucaaagccgg aaccgucc                48

<210> SEQ ID NO 15
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (6)..(6)
<223> OTHER INFORMATION: 2'-OMe substituted nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
```

```
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 15
ggacggauuu aaucgccgua gaaaagcaug ucaaagccgg aaccgucc                   48

<210> SEQ ID NO 16
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (7)..(7)
<223> OTHER INFORMATION: 2'-OMe substituted nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide
```

-continued

<400> SEQUENCE: 16
ggacggauuu aaucgccgua gaaaagcaug ucaaagccgg aaccgucc        48

<210> SEQ ID NO 17
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(8)
<223> OTHER INFORMATION: 2'-OMe substituted nucleotide
<220> FEATURE:
<221> NAME/KEY: modified_base
<222> LOCATION: (9)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 17
ggacggauuu aaucgccgua gaaaagcaug ucaaagccgg aaccgucc        48

<210> SEQ ID NO 18
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(8)
<223> OTHER INFORMATION: modified 2'-fluoro nucleotide -continued

```
<220> FEATURE:
<221> NAME/KEY: modified_base
<222> LOCATION: (9)..(9)
<223> OTHER INFORMATION: 2'-OMe substituted nucleotide
<220> FEATURE:
<221> NAME/KEY: modified_base
<222> LOCATION: (10)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 18
ggacggauuu aaucgccgua gaaaagcaug ucaaagccgg aaccgucc         48

<210> SEQ ID NO 19
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(9)
<223> OTHER INFORMATION: modified 2'-fluoro nucleotide
<220> FEATURE:
<221> NAME/KEY: modified_base
<222> LOCATION: (10)..(10)
<223> OTHER INFORMATION: 2'-OMe substituted nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
```

```
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 19
ggacggauuu aaucgccgua gaaaagcaug ucaaagccgg aaccgucc                48

<210> SEQ ID NO 20
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (11)..(11)
<223> OTHER INFORMATION: 2'-OMe substituted nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
```

```
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 20
ggacggauuu aaucgccgua gaaaagcaug ucaaagccgg aaccgucc                    48

<210> SEQ ID NO 21
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(13)
<223> OTHER INFORMATION: modified 2'-fluoro nucleotide
<220> FEATURE:
<221> NAME/KEY: modified_base
<222> LOCATION: (14)..(14)
<223> OTHER INFORMATION: 2'-OMe substituted nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 21
ggacggauuu aaucgccgua gaaaagcaug ucaaagccgg aaccgucc                    48

<210> SEQ ID NO 22
<211> LENGTH: 48
<212> TYPE: RNA
<213> ORGANISM: Artificial
<220> FEATURE:
<223> OTHER INFORMATION: Synthetic aptamer
<220> FEATURE:
```

<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (15)..(15)
<223> OTHER INFORMATION: 2'-OMe substituted nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 22
ggacggauuu aaucgccgua gaaaagcaug ucaaagccgg aaccgucc         48

<210> SEQ ID NO 23
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(16)
<223> OTHER INFORMATION: 2'-OMe substituted nucleotide
<220> FEATURE:
<221> NAME/KEY: modified_base
<222> LOCATION: (17)..(17)
<223> OTHER INFORMATION: modified 2'-fluoro nucleotide

```
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 23
ggacggauuu aaucgccgua gaaaagcaug ucaaagccgg aaccgucc                    48

<210> SEQ ID NO 24
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (18)..(18)
<223> OTHER INFORMATION: 2'-OMe substituted nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
```

<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 24
ggacggauuu aaucgccgua gaaaagcaug ucaaagccgg aaccgucc          48

<210> SEQ ID NO 25
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: 2'-OMe substituted nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 25
ggacggauuu aaucgccgua gaaaagcaug ucaaagccgg aaccgucc          48

<210> SEQ ID NO 26
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base -continued

```
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (20)..(20)
<223> OTHER INFORMATION: 2'-OMe substituted nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 26
ggacggauuu aaucgccgua gaaaagcaug ucaaagccgg aaccgucc          48

<210> SEQ ID NO 27
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
```

```
<221> NAME/KEY: modified_base
<222> LOCATION: (21)..(21)
<223> OTHER INFORMATION: 2'-OMe substituted nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 27
ggacggauuu aaucgccgua gaaaagcaug ucaaagccgg aaccgucc                         48

<210> SEQ ID NO 28
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (22)..(22)
<223> OTHER INFORMATION: 2'-OMe substituted nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
```

-continued

```
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 28
ggacggauuu aaucgccgua gaaaagcaug ucaaagccgg aaccgucc        48

<210> SEQ ID NO 29
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (23)..(23)
<223> OTHER INFORMATION: 2'-OMe substituted nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 29
ggacggauuu aaucgccgua gaaaagcaug ucaaagccgg aaccgucc        48

<210> SEQ ID NO 30
<211> LENGTH: 48
<212> TYPE: RNA
<213> ORGANISM: Artificial
<220> FEATURE:
```

```
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (24)..(24)
<223> OTHER INFORMATION: 2'-OMe substituted nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (45)..(45)
<223> OTHER INFORMATION: natural 2'-OH (RNA) nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 30
ggacggauuu aaucgccgua gaaaagcaug ucaaagccgg aaccgucc        48

<210> SEQ ID NO 31
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
```

```
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (25)..(25)
<223> OTHER INFORMATION: 2'-OMe substituted nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 31
ggacggauuu aaucgccgua gaaaagcaug ucaaagccgg aaccgucc         48

<210> SEQ ID NO 32
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (26)..(26)
<223> OTHER INFORMATION: 2'-OMe substituted nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
```

```
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 32
ggacggauuu aaucgccgua gaaaagcaug ucaaagccgg aaccgucc          48

<210> SEQ ID NO 33
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: 2'-OMe substituted nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 33
ggacggauuu aaucgccgua gaaaagcaug ucaaagccgg aaccgucc          48

<210> SEQ ID NO 34
<211> LENGTH: 48
```

```
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (28)..(28)
<223> OTHER INFORMATION: 2'-OMe substituted nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 34
ggacggauuu aaucgccgua gaaaagcaug ucaaagccgg aaccgucc          48

<210> SEQ ID NO 35
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
```

```
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (30)..(30)
<223> OTHER INFORMATION: 2'-OMe substituted nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 35
ggacggauuu aaucgccgua gaaaagcaug ucaaagccgg aaccgucc            48

<210> SEQ ID NO 36
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
```

<222> LOCATION: (33)..(33)
<223> OTHER INFORMATION: 2'-OMe substituted nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 36
ggacggauuu aaucgccgua gaaaagcaug ucaaagccgg aaccgucc       48

<210> SEQ ID NO 37
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (35)..(35)
<223> OTHER INFORMATION: 2'-OMe substituted nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 37
ggacggauuu aaucgccgua gaaaagcaug ucaaagccgg aaccgucc       48

<210> SEQ ID NO 38
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (36)..(36)
<223> OTHER INFORMATION: 2'-OMe substituted nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 38
ggacggauuu aaucgccgua gaaaagcaug ucaaagccgg aaccgucc                48

<210> SEQ ID NO 39
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide

```
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(37)
<223> OTHER INFORMATION: 2'-OMe substituted nucleotide
<220> FEATURE:
<221> NAME/KEY: modified_base
<222> LOCATION: (38)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 39
ggacggauuu aaucgccgua gaaaagcaug ucaaagccgg aaccgucc                48

<210> SEQ ID NO 40
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
```

-continued

<223> OTHER INFORMATION: modified 2'-fluoro nucleotide
<220> FEATURE:
<221> NAME/KEY: modified_base
<222> LOCATION: (37)..(37)
<223> OTHER INFORMATION: modified 2'-fluoro nucleotide
<220> FEATURE:
<221> NAME/KEY: modified_base
<222> LOCATION: (38)..(38)
<223> OTHER INFORMATION: 2'-OMe substituted nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 40
ggacggauuu aaucgccgua gaaaagcaug ucaaagccgg aaccgucc        48

<210> SEQ ID NO 41
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (39)..(39)
<223> OTHER INFORMATION: 2'-OMe substituted nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 41
ggacggauuu aaucgccgua gaaaagcaug ucaaagccgg aaccgucc        48

<210> SEQ ID NO 42
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (40)..(40)
<223> OTHER INFORMATION: 2'-OMe substituted nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 42
ggacggauuu aaucgccgua gaaaagcaug ucaaagccgg aaccgucc        48

<210> SEQ ID NO 43
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:

<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (41)..(41)
<223> OTHER INFORMATION: 2'-OMe substituted nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 43
ggacggauuu aaucgccgua gaaaagcaug ucaaagccgg aaccgucc        48

<210> SEQ ID NO 44
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide

```
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (42)..(42)
<223> OTHER INFORMATION: 2'-OMe substituted nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 44
ggacggauuu aaucgccgua gaaaagcaug ucaaagccgg aaccgucc                    48

<210> SEQ ID NO 45
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(43)
<223> OTHER INFORMATION: 2'-OMe substituted nucleotide
<220> FEATURE:
<221> NAME/KEY: modified_base
<222> LOCATION: (44)..(44)
<223> OTHER INFORMATION: modified 2'-fluoro nucleotide
<220> FEATURE:
<221> NAME/KEY: modified_base
<222> LOCATION: (46)..(48)
```

-continued

<223> OTHER INFORMATION: modified 2'-fluoro nucleotide

<400> SEQUENCE: 45
ggacggauuu aaucgccgua gaaaagcaug ucaaagccgg aaccgucc      48

<210> SEQ ID NO 46
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(43)
<223> OTHER INFORMATION: modified 2'-fluoro nucleotide
<220> FEATURE:
<221> NAME/KEY: modified_base
<222> LOCATION: (44)..(44)
<223> OTHER INFORMATION: 2'-OMe substituted nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 46
ggacggauuu aaucgccgua gaaaagcaug ucaaagccgg aaccgucc      48

<210> SEQ ID NO 47
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (45)..(45)
<223> OTHER INFORMATION: 2'-OMe substituted nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 47
ggacggauuu aaucgccgua gaaaagcaug ucaaagccgg aaccgucc                48

<210> SEQ ID NO 48
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:

<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (42)..(42)
<223> OTHER INFORMATION: natural 2'-OH (RNA) nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(46)
<223> OTHER INFORMATION: 2'-OMe substituted nucleotide
<220> FEATURE:
<221> NAME/KEY: modified_base
<222> LOCATION: (47)..(48)
<223> OTHER INFORMATION: modified 2'-fluoro nucleotide

<400> SEQUENCE: 48
ggacggauuu aaucgccgua gaaaagcaug ucaaagccgg aaccgucc         48

<210> SEQ ID NO 49
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(46)
<223> OTHER INFORMATION: modified 2'-fluoro nucleotide
<220> FEATURE:
<221> NAME/KEY: modified_base
<222> LOCATION: (47)..(47)
<223> OTHER INFORMATION: 2'-OMe substituted nucleotide
<220> FEATURE:
<221> NAME/KEY: modified_base
<222> LOCATION: (48)..(48)
<223> OTHER INFORMATION: modified 2'-fluoro nucleotide

<400> SEQUENCE: 49
ggacggauuu aaucgccgua gaaaagcaug ucaaagccgg aaccgucc          48

<210> SEQ ID NO 50
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(47)
<223> OTHER INFORMATION: modified 2'-fluoro nucleotide
<220> FEATURE:
<221> NAME/KEY: modified_base
<222> LOCATION: (48)..(48)
<223> OTHER INFORMATION: 2'-OMe substituted nucleotide

<400> SEQUENCE: 50
ggacggauuu aaucgccgua gaaaagcaug ucaaagccgg aaccgucc          48

<210> SEQ ID NO 51

```
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (1)..(3)
<223> OTHER INFORMATION: 2'-OMe substituted nucleotide
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (5)..(7)
<223> OTHER INFORMATION: 2'-OMe substituted nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (15)..(15)
<223> OTHER INFORMATION: 2'-OMe substituted nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (18)..(18)
<223> OTHER INFORMATION: 2'-OMe substituted nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (20)..(21)
<223> OTHER INFORMATION: 2'-OMe substituted nucleotide
<220> FEATURE:
<221> NAME/KEY: modified_base
<222> LOCATION: (23)..(24)
<223> OTHER INFORMATION: 2'-OMe substituted nucleotide
<220> FEATURE:
<221> NAME/KEY: modified_base
<222> LOCATION: (26)..(26)
<223> OTHER INFORMATION: 2'-OMe substituted nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (28)..(28)
<223> OTHER INFORMATION: 2'-OMe substituted nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (30)..(30)
<223> OTHER INFORMATION: 2'-OMe substituted nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (33)..(33)
<223> OTHER INFORMATION: 2'-OMe substituted nucleotide
<220> FEATURE:
<221> NAME/KEY: modified_base
```

<222> LOCATION: (36)..(36)
<223> OTHER INFORMATION: 2'-OMe substituted nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (39)..(41)
<223> OTHER INFORMATION: 2'-OMe substituted nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (45)..(45)
<223> OTHER INFORMATION: 2'-OMe substituted nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 51
ggacggauuu aaucgccgua gaaaagcaug ucaaagccgg aaccgucc          48

<210> SEQ ID NO 52
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: modified 2'-fluoro nucleotide
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:

```
<221> NAME/KEY: modified_base
<222> LOCATION: (46)..(48)
<223> OTHER INFORMATION: modified 2'-fluoro nucleotide

<400> SEQUENCE: 52
ggacggauuu aaucgccgua gaaaagcaug ucaaagccgg aaccgucc          48

<210> SEQ ID NO 53
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (2)..(2)
<223> OTHER INFORMATION: modified 2'-fluoro nucleotide
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 53
ggacggauuu aaucgccgua gaaaagcaug ucaaagccgg aaccgucc          48

<210> SEQ ID NO 54
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (3)..(4)
<223> OTHER INFORMATION: modified 2'-fluoro nucleotide
```

-continued

```
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 54
ggacggauuu aaucgccgua gaaaagcaug ucaaagccgg aaccgucc                    48

<210> SEQ ID NO 55
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(5)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
```

<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 55
ggacggauuu aaucgccgua gaaaagcaug ucaaagccgg aaccgucc                48

<210> SEQ ID NO 56
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (6)..(6)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 56
ggacggauuu aaucgccgua gaaaagcaug ucaaagccgg aaccgucc        48

<210> SEQ ID NO 57
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (7)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 57
ggacggauuu aaucgccgua gaaaagcaug ucaaagccgg aaccgucc        48

<210> SEQ ID NO 58
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(11)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:

```
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 58
ggacggauuu aaucgccgua gaaaagcaug ucaaagccgg aaccgucc            48

<210> SEQ ID NO 59
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (12)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
```

```
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 59
ggacggauuu aaucgccgua gaaaagcaug ucaaagccgg aaccgucc                48

<210> SEQ ID NO 60
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 60
ggacggauuu aaucgccgua gaaaagcaug ucaaagccgg aaccgucc                48

<210> SEQ ID NO 61
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
```

<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 61
ggacggauuu aaucgccgua gaaaagcaug ucaaagccgg aaccgucc        48

<210> SEQ ID NO 62
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(20)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base

```
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 62
ggacggauuu aaucgccgua gaaaagcaug ucaaagccgg aaccgucc       48

<210> SEQ ID NO 63
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (21)..(21)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 63
ggacggauuu aaucgccgua gaaaagcaug ucaaagccgg aaccgucc       48

<210> SEQ ID NO 64
<211> LENGTH: 48
<212> TYPE: RNA
```

```
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (22)..(22)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 64
ggacggauuu aaucgccgua gaaaagcaug ucaaagccgg aaccgucc                    48

<210> SEQ ID NO 65
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
```

-continued

```
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (23)..(23)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 65
ggacggauuu aaucgccgua gaaaagcaug ucaaagccgg aaccgucc        48

<210> SEQ ID NO 66
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (24)..(24)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
```

<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 66
ggacggauuu aaucgccgua gaaaagcaug ucaaagccgg aaccgucc        48

<210> SEQ ID NO 67
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (25)..(25)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 67
ggacggauuu aaucgccgua gaaaagcaug ucaaagccgg aaccgucc        48

```
<210> SEQ ID NO 68
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (26)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 68
ggacggauuu aaucgccgua gaaaagcaug ucaaagccgg aaccgucc        48

<210> SEQ ID NO 69
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
```

```
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 69
ggacggauuu aaucgccgua gaaaagcaug ucaaagccgg aaccgucc                48

<210> SEQ ID NO 70
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 70
ggacggauuu aaucgccgua gaaaagcaug ucaaagccgg aaccgucc                48
```

```
<210> SEQ ID NO 71
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(33)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 71
ggacggauuu aaucgccgua gaaaagcaug ucaaagccgg aaccgucc                48

<210> SEQ ID NO 72
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
```

```
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (36)..(38)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 72
ggacggauuu aaucgccgua gaaaagcaug ucaaagccgg aaccgucc            48

<210> SEQ ID NO 73
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(39)
<223> OTHER INFORMATION: modified 2'-fluoro nucleotide
<220> FEATURE:
<221> NAME/KEY: modified_base
```

-continued

```
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 73
ggacggauuu aaucgccgua gaaaagcaug ucaaagccgg aaccgucc          48

<210> SEQ ID NO 74
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (40)..(40)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 74
ggacggauuu aaucgccgua gaaaagcaug ucaaagccgg aaccgucc          48

<210> SEQ ID NO 75
<211> LENGTH: 48
<212> TYPE: RNA
<213> ORGANISM: Artificial
<220> FEATURE:
<223> OTHER INFORMATION: Synthetic aptamer
<220> FEATURE:
```

<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (41)..(41)
<223> OTHER INFORMATION: modified 2'-fluoro nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 75
ggacggauuu aaucgccgua gaaaagcaug ucaaagccgg aaccgucc        48

<210> SEQ ID NO 76
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide

```
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (42)..(44)
<223> OTHER INFORMATION: modified 2'-fluoro nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 76
ggacggauuu aaucgccgua gaaaagcaug ucaaagccgg aaccgucc          48

<210> SEQ ID NO 77
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (43)..(48)
<223> OTHER INFORMATION: modified 2'-fluoro nucleotide

<400> SEQUENCE: 77
```
ggacggauuu aaucgccgua gaaaagcaug ucaaagccgg aaccgucc          48

<210> SEQ ID NO 78
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (1)..(3)
<223> OTHER INFORMATION: 2'-OMe substituted nucleotide
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (5)..(7)
<223> OTHER INFORMATION: 2'-OMe substituted nucleotide
<220> FEATURE:
<221> NAME/KEY: modified_base
<222> LOCATION: (8)..(11)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (15)..(15)
<223> OTHER INFORMATION: 2'-OMe substituted nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (18)..(18)
<223> OTHER INFORMATION: 2'-OMe substituted nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (20)..(21)
<223> OTHER INFORMATION: 2'-OMe substituted nucleotide
<220> FEATURE:
<221> NAME/KEY: modified_base
<222> LOCATION: (23)..(24)
<223> OTHER INFORMATION: 2'-OMe substituted nucleotide
<220> FEATURE:
<221> NAME/KEY: modified_base
<222> LOCATION: (25)..(25)
<223> OTHER INFORMATION: modified 2'-fluoro nucleotide
<220> FEATURE:
<221> NAME/KEY: modified_base
<222> LOCATION: (26)..(26)
<223> OTHER INFORMATION: 2'-OMe substituted nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (28)..(28)
<223> OTHER INFORMATION: 2'-OMe substituted nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (30)..(30)
<223> OTHER INFORMATION: 2'-OMe substituted nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (33)..(33)
<223> OTHER INFORMATION: 2'-OMe substituted nucleotide
<220> FEATURE:
<221> NAME/KEY: modified_base
<222> LOCATION: (36)..(36)
<223> OTHER INFORMATION: 2'-OMe substituted nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (39)..(41)
<223> OTHER INFORMATION: 2'-OMe substituted nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (45)..(45)
<223> OTHER INFORMATION: 2'-OMe substituted nucleotide
<220> FEATURE:
<221> NAME/KEY: modified_base
<222> LOCATION: (46)..(48)
<223> OTHER INFORMATION: modified 2'-fluoro nucleotide

<400> SEQUENCE: 78
ggacggauuu aaucgccgua gaaaagcaug ucaaagccgg aaccgucc         48

<210> SEQ ID NO 79
<211> LENGTH: 42
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (1)..(4)
<223> OTHER INFORMATION: 2'-OMe substituted nucleotide
<220> FEATURE:
<221> NAME/KEY: modified_base
<222> LOCATION: (5)..(7)
<223> OTHER INFORMATION: modified 2'-fluoro nucleotide
<220> FEATURE:
<221> NAME/KEY: modified_base
<222> LOCATION: (10)..(11)
<223> OTHER INFORMATION: modified 2'-fluoro nucleotide
<220> FEATURE:
<221> NAME/KEY: modified_base
<222> LOCATION: (12)..(12)
<223> OTHER INFORMATION: 2'-OMe substituted nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (15)..(15)
<223> OTHER INFORMATION: 2'-OMe substituted nucleotide
<220> FEATURE:
<221> NAME/KEY: modified_base
<222> LOCATION: (16)..(16)
<223> OTHER INFORMATION: modified 2'-fluoro nucleotide
<220> FEATURE:
<221> NAME/KEY: modified_base
<222> LOCATION: (17)..(18)
<223> OTHER INFORMATION: 2'-OMe substituted nucleotide
<220> FEATURE:
<221> NAME/KEY: modified_base
<222> LOCATION: (20)..(21)
<223> OTHER INFORMATION: 2'-OMe substituted nucleotide
<220> FEATURE:

-continued

```
<221> NAME/KEY: modified_base
<222> LOCATION: (23)..(23)
<223> OTHER INFORMATION: 2'-OMe substituted nucleotide
<220> FEATURE:
<221> NAME/KEY: modified_base
<222> LOCATION: (24)..(24)
<223> OTHER INFORMATION: modified 2'-fluoro nucleotide
<220> FEATURE:
<221> NAME/KEY: modified_base
<222> LOCATION: (25)..(25)
<223> OTHER INFORMATION: 2'-OMe substituted nucleotide
<220> FEATURE:
<221> NAME/KEY: modified_base
<222> LOCATION: (26)..(26)
<223> OTHER INFORMATION: modified 2'-fluoro nucleotide
<220> FEATURE:
<221> NAME/KEY: modified_base
<222> LOCATION: (27)..(27)
<223> OTHER INFORMATION: 2'-OMe substituted nucleotide
<220> FEATURE:
<221> NAME/KEY: modified_base
<222> LOCATION: (28)..(29)
<223> OTHER INFORMATION: modified 2'-fluoro nucleotide
<220> FEATURE:
<221> NAME/KEY: modified_base
<222> LOCATION: (30)..(30)
<223> OTHER INFORMATION: 2'-OMe substituted nucleotide
<220> FEATURE:
<221> NAME/KEY: modified_base
<222> LOCATION: (33)..(33)
<223> OTHER INFORMATION: 2'-OMe substituted nucleotide
<220> FEATURE:
<221> NAME/KEY: modified_base
<222> LOCATION: (34)..(35)
<223> OTHER INFORMATION: modified 2'-fluoro nucleotide
<220> FEATURE:
<221> NAME/KEY: modified_base
<222> LOCATION: (36)..(38)
<223> OTHER INFORMATION: 2'-OMe substituted nucleotide
<220> FEATURE:
<221> NAME/KEY: modified_base
<222> LOCATION: (40)..(42)
<223> OTHER INFORMATION: modified 2'-fluoro nucleotide

<400> SEQUENCE: 79
gggauuuaau cgccguagaa aagcauguca aagccggaac cc                    42

<210> SEQ ID NO 80
<211> LENGTH: 42
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (1)..(4)
<223> OTHER INFORMATION: 2'-OMe substituted nucleotide
<220> FEATURE:
<221> NAME/KEY: modified_base
<222> LOCATION: (5)..(8)
<223> OTHER INFORMATION: modified 2'-fluoro nucleotide
<220> FEATURE:
<221> NAME/KEY: modified_base
<222> LOCATION: (10)..(11)
<223> OTHER INFORMATION: modified 2'-fluoro nucleotide
<220> FEATURE:
<221> NAME/KEY: modified_base
<222> LOCATION: (12)..(12)
<223> OTHER INFORMATION: 2'-OMe substituted nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (15)..(15)
<223> OTHER INFORMATION: 2'-OMe substituted nucleotide
```

```
<220> FEATURE:
<221> NAME/KEY: modified_base
<222> LOCATION: (16)..(16)
<223> OTHER INFORMATION: modified 2'-fluoro nucleotide
<220> FEATURE:
<221> NAME/KEY: modified_base
<222> LOCATION: (17)..(18)
<223> OTHER INFORMATION: 2'-OMe substituted nucleotide
<220> FEATURE:
<221> NAME/KEY: modified_base
<222> LOCATION: (20)..(21)
<223> OTHER INFORMATION: 2'-OMe substituted nucleotide
<220> FEATURE:
<221> NAME/KEY: modified_base
<222> LOCATION: (22)..(22)
<223> OTHER INFORMATION: modified 2'-fluoro nucleotide
<220> FEATURE:
<221> NAME/KEY: modified_base
<222> LOCATION: (23)..(23)
<223> OTHER INFORMATION: 2'-OMe substituted nucleotide
<220> FEATURE:
<221> NAME/KEY: modified_base
<222> LOCATION: (24)..(24)
<223> OTHER INFORMATION: modified 2'-fluoro nucleotide
<220> FEATURE:
<221> NAME/KEY: modified_base
<222> LOCATION: (25)..(25)
<223> OTHER INFORMATION: 2'-OMe substituted nucleotide
<220> FEATURE:
<221> NAME/KEY: modified_base
<222> LOCATION: (26)..(26)
<223> OTHER INFORMATION: modified 2'-fluoro nucleotide
<220> FEATURE:
<221> NAME/KEY: modified_base
<222> LOCATION: (27)..(27)
<223> OTHER INFORMATION: 2'-OMe substituted nucleotide
<220> FEATURE:
<221> NAME/KEY: modified_base
<222> LOCATION: (28)..(29)
<223> OTHER INFORMATION: modified 2'-fluoro nucleotide
<220> FEATURE:
<221> NAME/KEY: modified_base
<222> LOCATION: (30)..(30)
<223> OTHER INFORMATION: 2'-OMe substituted nucleotide
<220> FEATURE:
<221> NAME/KEY: modified_base
<222> LOCATION: (33)..(33)
<223> OTHER INFORMATION: 2'-OMe substituted nucleotide
<220> FEATURE:
<221> NAME/KEY: modified_base
<222> LOCATION: (34)..(35)
<223> OTHER INFORMATION: modified 2'-fluoro nucleotide
<220> FEATURE:
<221> NAME/KEY: modified_base
<222> LOCATION: (36)..(38)
<223> OTHER INFORMATION: 2'-OMe substituted nucleotide
<220> FEATURE:
<221> NAME/KEY: modified_base
<222> LOCATION: (40)..(42)
<223> OTHER INFORMATION: modified 2'-fluoro nucleotide

<400> SEQUENCE: 80
gggauuuaau cgccguagaa aagcauguca aagccggaac cc          42

<210> SEQ ID NO 81
<211> LENGTH: 51
<212> TYPE: RNA
<213> ORGANISM: Artificial
<220> FEATURE:
<223> OTHER INFORMATION: Synthetic aptamer
<220> FEATURE:
<221> NAME/KEY: misc_feature
<222> LOCATION: (4)..(5)
<223> OTHER INFORMATION: absent or G
<220> FEATURE:
<221> NAME/KEY: misc_feature
<222> LOCATION: (6)..(6)
```

```
<223> OTHER INFORMATION: absent or A
<220> FEATURE:
<221> NAME/KEY: misc_feature
<222> LOCATION: (7)..(7)
<223> OTHER INFORMATION: absent or C
<220> FEATURE:
<221> NAME/KEY: misc_feature
<222> LOCATION: (8)..(9)
<223> OTHER INFORMATION: absent or G
<220> FEATURE:
<221> NAME/KEY: misc_feature
<222> LOCATION: (10)..(10)
<223> OTHER INFORMATION: absent or A
<220> FEATURE:
<221> NAME/KEY: misc_feature
<222> LOCATION: (11)..(12)
<223> OTHER INFORMATION: absent or U
<220> FEATURE:
<221> NAME/KEY: misc_feature
<222> LOCATION: (48)..(48)
<223> OTHER INFORMATION: absent or G
<220> FEATURE:
<221> NAME/KEY: misc_feature
<222> LOCATION: (49)..(49)
<223> OTHER INFORMATION: absent or U
<220> FEATURE:
<221> NAME/KEY: misc_feature
<222> LOCATION: (50)..(50)
<223> OTHER INFORMATION: absent or C

<400> SEQUENCE: 81
aaannnnnnn nnuaaucgcc guagaaaagc augucaaagc cggaaccnnn c         51

<210> SEQ ID NO 82
<211> LENGTH: 52
<212> TYPE: RNA
<213> ORGANISM: Artificial
<220> FEATURE:
<223> OTHER INFORMATION: Synthetic aptamer
<220> FEATURE:
<221> NAME/KEY: misc_feature
<222> LOCATION: (5)..(6)
<223> OTHER INFORMATION: absent or G
<220> FEATURE:
<221> NAME/KEY: misc_feature
<222> LOCATION: (7)..(7)
<223> OTHER INFORMATION: absent or A
<220> FEATURE:
<221> NAME/KEY: misc_feature
<222> LOCATION: (8)..(8)
<223> OTHER INFORMATION: absent or C
<220> FEATURE:
<221> NAME/KEY: misc_feature
<222> LOCATION: (9)..(10)
<223> OTHER INFORMATION: absent or G
<220> FEATURE:
<221> NAME/KEY: misc_feature
<222> LOCATION: (11)..(11)
<223> OTHER INFORMATION: absent or A
<220> FEATURE:
<221> NAME/KEY: misc_feature
<222> LOCATION: (12)..(13)
<223> OTHER INFORMATION: absent or U
<220> FEATURE:
<221> NAME/KEY: misc_feature
<222> LOCATION: (49)..(49)
<223> OTHER INFORMATION: absent or G
<220> FEATURE:
<221> NAME/KEY: misc_feature
<222> LOCATION: (50)..(50)
<223> OTHER INFORMATION: absent or U
<220> FEATURE:
<221> NAME/KEY: misc_feature
<222> LOCATION: (51)..(51)
<223> OTHER INFORMATION: absent or C

<400> SEQUENCE: 82
```
aaagnnnnnn nnnuaaucgc cguagaaaag caugucaaag ccggaaccnn nc            52

<210> SEQ ID NO 83
<211> LENGTH: 51
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (1)..(3)
<223> OTHER INFORMATION: 2'-OMe substituted nucleotide
<220> FEATURE:
<221> NAME/KEY: modified_base
<222> LOCATION: (7)..(7)
<223> OTHER INFORMATION: modified 2'-fluoro nucleotide
<220> FEATURE:
<221> NAME/KEY: modified_base
<222> LOCATION: (11)..(13)
<223> OTHER INFORMATION: modified 2'-fluoro nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (19)..(20)
<223> OTHER INFORMATION: modified 2'-fluoro nucleotide
<220> FEATURE:
<221> NAME/KEY: modified_base
<222> LOCATION: (22)..(22)
<223> OTHER INFORMATION: modified 2'-fluoro nucleotide
<220> FEATURE:
<221> NAME/KEY: modified_base
<222> LOCATION: (30)..(30)
<223> OTHER INFORMATION: modified 2'-fluoro nucleotide
<220> FEATURE:
<221> NAME/KEY: modified_base
<222> LOCATION: (32)..(32)
<223> OTHER INFORMATION: modified 2'-fluoro nucleotide
<220> FEATURE:
<221> NAME/KEY: modified_base
<222> LOCATION: (34)..(35)
<223> OTHER INFORMATION: modified 2'-fluoro nucleotide
<220> FEATURE:
<221> NAME/KEY: modified_base
<222> LOCATION: (40)..(41)
<223> OTHER INFORMATION: modified 2'-fluoro nucleotide
<220> FEATURE:
<221> NAME/KEY: modified_base
<222> LOCATION: (46)..(47)
<223> OTHER INFORMATION: modified 2'-fluoro nucleotide
<220> FEATURE:
<221> NAME/KEY: modified_base
<222> LOCATION: (49)..(51)
<223> OTHER INFORMATION: modified 2'-fluoro nucleotide

<400> SEQUENCE: 83
aaaggacgga uuuaaucgcc guagaaaagc augucaaagc cggaaccguc c            51

<210> SEQ ID NO 84
<211> LENGTH: 45
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (1)..(7)
<223> OTHER INFORMATION: 2'-OMe substituted nucleotide
<220> FEATURE:
<221> NAME/KEY: modified_base
<222> LOCATION: (8)..(10)
<223> OTHER INFORMATION: modified 2'-fluoro nucleotide
<220> FEATURE:

```
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (15)..(15)
<223> OTHER INFORMATION: 2'-OMe substituted nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (18)..(18)
<223> OTHER INFORMATION: 2'-OMe substituted nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (20)..(21)
<223> OTHER INFORMATION: 2'-OMe substituted nucleotide
<220> FEATURE:
<221> NAME/KEY: modified_base
<222> LOCATION: (23)..(24)
<223> OTHER INFORMATION: 2'-OMe substituted nucleotide
<220> FEATURE:
<221> NAME/KEY: modified_base
<222> LOCATION: (26)..(26)
<223> OTHER INFORMATION: 2'-OMe substituted nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (28)..(28)
<223> OTHER INFORMATION: 2'-OMe substituted nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (30)..(30)
<223> OTHER INFORMATION: 2'-OMe substituted nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (33)..(33)
<223> OTHER INFORMATION: 2'-OMe substituted nucleotide
<220> FEATURE:
<221> NAME/KEY: modified_base
<222> LOCATION: (36)..(36)
<223> OTHER INFORMATION: 2'-OMe substituted nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (39)..(41)
<223> OTHER INFORMATION: 2'-OMe substituted nucleotide
<220> FEATURE:
<221> NAME/KEY: modified_base
<222> LOCATION: (43)..(45)
<223> OTHER INFORMATION: modified 2'-fluoro nucleotide

<400> SEQUENCE: 84
aaagggauuu aaucgccgua gaaaagcaug ucaaagccgg aaccc            45
```

-continued

```
<210> SEQ ID NO 85
<211> LENGTH: 48
<212> TYPE: RNA
<213> ORGANISM: Artificial
<220> FEATURE:
<223> OTHER INFORMATION: Synthetic aptamer
<220> FEATURE:
<221> NAME/KEY: modified_base
<222> LOCATION: (1)..(3)
<223> OTHER INFORMATION: 2'-OMe substituted nucleotide
<220> FEATURE:
<221> NAME/KEY: modified_base
<222> LOCATION: (4)..(4)
<223> OTHER INFORMATION: modified 2'-fluoro nucleotide
<220> FEATURE:
<221> NAME/KEY: modified_base
<222> LOCATION: (5)..(7)
<223> OTHER INFORMATION: 2'-OMe substituted nucleotide
<220> FEATURE:
<221> NAME/KEY: modified_base
<222> LOCATION: (8)..(10)
<223> OTHER INFORMATION: modified 2'-fluoro nucleotide
<220> FEATURE:
<221> NAME/KEY: modified_base
<222> LOCATION: (13)..(14)
<223> OTHER INFORMATION: modified 2'-fluoro nucleotide
<220> FEATURE:
<221> NAME/KEY: modified_base
<222> LOCATION: (15)..(15)
<223> OTHER INFORMATION: 2'-OMe substituted nucleotide
<220> FEATURE:
<221> NAME/KEY: modified_base
<222> LOCATION: (16)..(17)
<223> OTHER INFORMATION: modified 2'-fluoro nucleotide
<220> FEATURE:
<221> NAME/KEY: modified_base
<222> LOCATION: (18)..(18)
<223> OTHER INFORMATION: 2'-OMe substituted nucleotide
<220> FEATURE:
<221> NAME/KEY: modified_base
<222> LOCATION: (19)..(19)
<223> OTHER INFORMATION: modified 2'-fluoro nucleotide
<220> FEATURE:
<221> NAME/KEY: modified_base
<222> LOCATION: (20)..(21)
<223> OTHER INFORMATION: 2'-OMe substituted nucleotide
<220> FEATURE:
<221> NAME/KEY: modified_base
<222> LOCATION: (23)..(24)
<223> OTHER INFORMATION: 2'-OMe substituted nucleotide
<220> FEATURE:
<221> NAME/KEY: modified_base
<222> LOCATION: (26)..(26)
<223> OTHER INFORMATION: 2'-OMe substituted nucleotide
<220> FEATURE:
<221> NAME/KEY: modified_base
<222> LOCATION: (27)..(27)
<223> OTHER INFORMATION: modified 2'-fluoro nucleotide
<220> FEATURE:
<221> NAME/KEY: modified_base
<222> LOCATION: (28)..(28)
<223> OTHER INFORMATION: 2'-OMe substituted nucleotide
<220> FEATURE:
<221> NAME/KEY: modified_base
<222> LOCATION: (29)..(29)
<223> OTHER INFORMATION: modified 2'-fluoro nucleotide
<220> FEATURE:
<221> NAME/KEY: modified_base
<222> LOCATION: (30)..(30)
<223> OTHER INFORMATION: 2'-OMe substituted nucleotide
<220> FEATURE:
<221> NAME/KEY: modified_base
<222> LOCATION: (31)..(32)
<223> OTHER INFORMATION: modified 2'-fluoro nucleotide
<220> FEATURE:
<221> NAME/KEY: modified_base
<222> LOCATION: (33)..(33)
<223> OTHER INFORMATION: 2'-OMe substituted nucleotide
```

```
<220> FEATURE:
<221> NAME/KEY: modified_base
<222> LOCATION: (36)..(36)
<223> OTHER INFORMATION: 2'-OMe substituted nucleotide
<220> FEATURE:
<221> NAME/KEY: modified_base
<222> LOCATION: (37)..(38)
<223> OTHER INFORMATION: modified 2'-fluoro nucleotide
<220> FEATURE:
<221> NAME/KEY: modified_base
<222> LOCATION: (39)..(41)
<223> OTHER INFORMATION: 2'-OMe substituted nucleotide
<220> FEATURE:
<221> NAME/KEY: modified_base
<222> LOCATION: (43)..(44)
<223> OTHER INFORMATION: modified 2'-fluoro nucleotide
<220> FEATURE:
<221> NAME/KEY: modified_base
<222> LOCATION: (45)..(45)
<223> OTHER INFORMATION: 2'-OMe substituted nucleotide
<220> FEATURE:
<221> NAME/KEY: modified_base
<222> LOCATION: (46)..(48)
<223> OTHER INFORMATION: modified 2'-fluoro nucleotide
<220> FEATURE:
<221> NAME/KEY: misc_feature
<222> LOCATION: (48)..(48)
<223> OTHER INFORMATION: 3' i-dT tail

<400> SEQUENCE: 85
ggacggauuu aaucgccgua gaaaagcaug ucaaagccgg aaccgucc          48
```

APTAMERS AGAINST EGFR AND THERAPEUTIC USES THEREOF

CROSS-REFERENCE TO RELATED APPLICATIONS

The present application is a U.S. National Stage entry under 35 U.S.C. § 371 of International Application No. PCT/GB2015/051812 filed on Jun. 23, 2015, designating the United States of America and published in English on Dec. 30, 2015, which in turn claims priority to Great Britain Patent Application 1411150.4 filed on Jun. 23, 2014, each of which is hereby incorporated by reference in its entirety.

FIELD OF THE INVENTION

The invention relates to novel aptamers, in particular aptamers which are capable of binding to EGFR. The invention also relates to cancer cell binding complexes comprising said aptamers and the use of said cancer cell binding complexes in the treatment of cancer.

BACKGROUND OF THE INVENTION

Cancer is a group of diseases involving abnormal cell growth with the potential to invade or spread to other parts of the body. In 2012, cancer occurred in about 14.1 million people. It caused about 8.2 million deaths or 14.6% of all human deaths. The most common types of cancer in males are lung cancer, prostate cancer, colorectal cancer and stomach cancer. In females the most common types are breast cancer, colorectal cancer, and lung cancer, and cervical cancer.

The epidermal growth factor receptor (EGFR), also known as ErbB-1 or HER1 in humans, is the cell-surface receptor for members of the epidermal growth factor family (EGF-family) of extracellular protein ligands. EGFR is a member of the ErbB family of receptors, a subfamily of four closely related receptor tyrosine kinases: EGFR (ErbB-1), HER2/c-neu (ErbB-2), Her 3 (ErbB-3) and Her 4 (ErbB-4).

Mutations affecting EGFR expression or activity could result in cancer. In particular, mutations that lead to EGFR overexpression (known as upregulation) or overactivity have been associated with a number of cancers, including lung cancer, anal cancers (such as colorectal cancer) and glioblastoma multiforme. These somatic mutations involving EGFR lead to its constant activation, which produces uncontrolled cell division. In glioblastoma a more or less specific mutation of EGFR, called EGFRvIII is often observed. Mutations, amplifications or misregulations of EGFR or family members are implicated in about 30% of all epithelial cancers.

An innovative approach to cancer treatment was disclosed in WO 2005/079423 which describes an immunity linker which contains two binding moieties. The first binding moiety is capable of binding to an immune response component of an individual. The second binding moiety is capable of binding to any compound or foreign material such as antigens, pathogens, chemicals, or endogenous materials such as altered cells found in cancer. The resultant effect of said immunity linker molecule is that the immune response of the individual is diverted from the pre-existing immune response of said individual towards the target, i.e. the cancer cell. Examples of said first binding moieties include compounds or agents which are recognised by the immune system of said individual as foreign and which would therefore trigger an immune response. One such example is the alpha-Gal epitope (i.e. galactosyl-alpha-1,3-galactosyl-beta-1,4-N-acetylglucosamine) which results in redirection of the natural human serum antibody Anti-alpha-galactosyl. Examples of said second binding moieties include antibodies and aptamers. Aptamers are oligonucleic acid or peptide molecules that bind to a specific target molecule. The principle of the method disclosed in WO 2005/079423 is that the second binding moiety (i.e. aptamer) of the linker molecule will bind to an epitope on a cancer cell and the presence of the first binding moiety (i.e. the alpha-Gal epitope) on the linker molecule will divert an immune response to the cancer cell resulting in effective destruction of the cancer cell.

Li et al (2011) PLoS One 6(6), 1-9 describes a series of anti-EGFR aptamers, including E07. A dissertion was presented by Viswatej Avutu in 2011 (repositories.lib.utexas.edu/bitstream/handle/2152/13407/Avutu-Bioch 10.pdf-?sequence=2) which describes a minimised variant of E07 known as MinE07 which has the following sequence:
5'-rGrGrA fCrGrG rAfUfU fUrArA fUfCrG fCfCrG fUrArG rArArA rArGfC rAfUrG fUfCrA rArArG fCfCrG rGrArA fCfCrG fUfCfC-3' (SEQ ID NO: 85), wherein "r" represents a natural 2'-OH (RNA) nucleotide and "f" represents a modified 2'-fluoro nucleotide. In this sequence there are 28 of 48 unmodified nucleotides which can lead to nuclease degradation when administered therapeutically.

There is therefore, a great need for alternative, therapeutically effective aptamers which not only retain the ability to bind to epitopes present on cancer cells, but which are also capable of withstanding degradation. Such aptamers will have great utility in binding complexes with agents capable of binding to an immune response component of an individual to provide effective anti-cancer therapies.

SUMMARY OF THE INVENTION

According to a first aspect of the invention, there is provided a ribonucleic acid molecule comprising a nucleotide sequence selected from:

$$\text{(SEQ ID NO: 1)}$$
$$5'-X_1X_2X_3\ X_4X_5X_6\ X_7X_8X_9\ U_{10}A_{11}A_{12}\ U_{13}C_{14}G_{15}\ C_{16}C_{17}G_{18}$$
$$U_{19}A_{20}G_{21}\ A_{22}A_{23}A_{24}\ A_{25}G_{26}C_{27}\ A_{28}U_{29}G_{30}\ U_{31}C_{32}A_{33}\ A_{34}A_{35}G_{36}$$
$$C_{37}C_{38}G_{39}\ G_{40}A_{41}A_{42}\ C_{43}C_{44}X_{45}\ X_{46}X_{47}C_{48}-3',$$

wherein $X_1$, $X_2$, $X_5$, $X_6$ and $X_{45}$ are either absent or G, $X_3$ and $X_7$ are either absent or A, $X_4$ and $X_{47}$ are either absent or C and $X_8$, $X_9$ and $X_{46}$ are either absent or U, such that when $X_7$-$X_9$ are each absent then at least one of $X_1$-$X_6$ must also be absent; and
optionally wherein the 2'-OH groups of one or more nucleotides, other than nucleotides 12 to 13, 17, 29, 31 to 32 and 34, may be substituted by a 2'-OMe group; and
optionally wherein the 2'-OH groups of one or more of the A and G nucleotides, other than nucleotides 34 and 35, may be substituted by a 2'-F group, with the proviso that when each of $X_1$-$X_9$ and $X_{45}$-$X_{47}$ are present then at least one nucleotide must contain one of said substitutions or said molecule must contain between 1 and 15 additional nucleotides.

According to a further aspect of the invention, there is provided a cancer cell binding complex which comprises an aptamer as defined herein conjugated, or otherwise linked, to an immunogenic molecule.

According to a further aspect of the invention, there is provided a pharmaceutical composition comprising at least one cancer cell binding complex as defined herein, together with one or more pharmaceutically acceptable excipients and optionally other therapeutic or prophylactic agents.

According to a further aspect of the invention, there is provided a cancer cell binding complex as defined herein for use in the treatment of cancer.

DETAILED DESCRIPTION OF THE INVENTION

Figure 1:
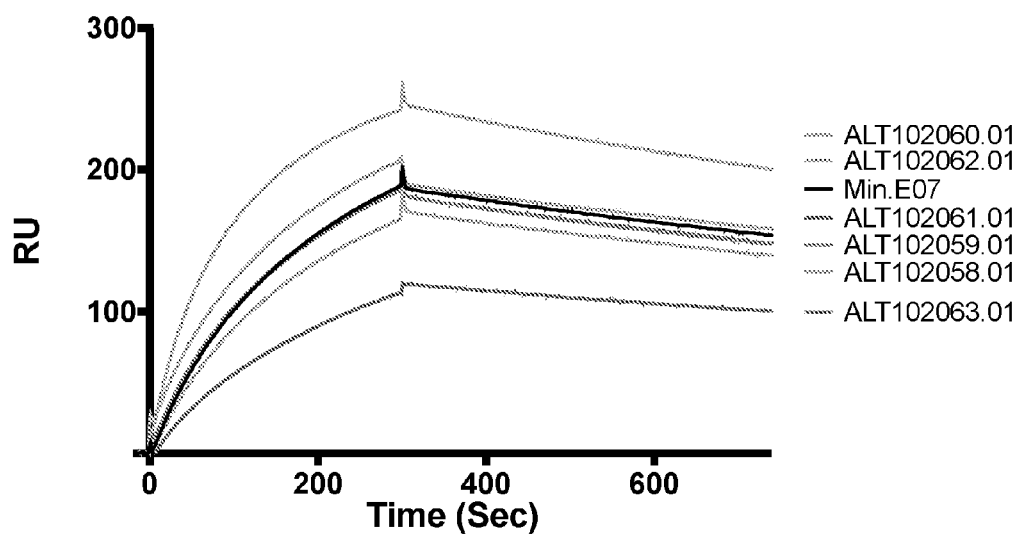
FIGS. 1 to 15 describe the results of the surface plasmon resonance assay (SPR) analysis with the aptamers of the invention.

According to a first aspect of the invention, there is provided a ribonucleic acid molecule comprising a nucleotide sequence selected from:

(SEQ ID NO: 1)
5'-$X_1X_2X_3$ $X_4X_5X_6$ $X_7X_8X_9$ $U_{10}A_{11}A_{12}$ $U_{13}C_{14}G_{15}$ $C_{16}C_{17}G_{18}$ $U_{19}A_{20}G_{21}$ $A_{22}A_{23}A_{24}$ $A_{25}G_{26}C_{27}$ $A_{28}U_{29}G_{30}$ $U_{31}C_{32}A_{33}$ $A_{34}A_{35}G_{36}$ $C_{37}C_{38}G_{39}$ $G_{40}A_{41}A_{42}$ $C_{43}C_{44}X_{45}$ $X_{46}X_{47}C_{48}$-3', wherein $X_1$, $X_2$, $X_5$, $X_6$ and $X_{45}$ are either absent or G, $X_3$ and $X_7$ are either absent or A, $X_4$ and $X_{47}$ are either absent or C and $X_8$, $X_9$ and $X_{46}$ are either absent or U, such that when $X_7$-$X_9$ are each absent then at least one of $X_1$-$X_6$ must also be absent; and optionally wherein the 2'-OH groups of one or more nucleotides, other than nucleotides 12 to 13, 17, 29, 31 to 32 and 34, may be substituted by a 2'-OMe group; and optionally wherein the 2'-OH groups of one or more of the A and G nucleotides, other than nucleotides 34 and 35, may be substituted by a 2'-F group, with the proviso that when each of $X_1$-$X_9$ and $X_{45}$-$X_{47}$ are present then at least one nucleotide must contain one of said substitutions or said molecule must contain between 1 and 15 additional nucleotides.

A significant number of aptamers within the scope of SEQ ID NO: 1 have surprisingly been found to bind to recombinant EGFR and/or EGFR cells and therefore provide a promising target for combining the aptamers with immune response generating moieties for the treatment of cancer (as set out in WO 2005/079423).

The intention of the proviso within the first aspect of the invention is to exclude the known E07 and MinE07 aptamers. The intention of the requirement for specific positional substitutions by 2'-OMe and 2'-F and that when $X_7$-$X_9$ are each absent then at least one of $X_1$-$X_6$ must also be absent, within the first aspect of the invention, is to exclude non-binding aptamers.

It will be appreciated that the numbering referred to in SEQ ID NO: 1 refer to the nucleotide positions 1 to 48.

Aptamer Modifications

In one embodiment, each of the 2'-OH groups of the C and U nucleotides within SEQ ID NO: 1 are modified to a 2'-F group. Thus, in a further embodiment, the ribonucleic acid molecule has a nucleotide sequence selected from:

(SEQ ID NO: 2)
5'-$X_1X_2X_3$ $X_4X_5X_6$ $X_7X_8X_9$ $fU_{10}A_{11}A_{12}$ $fU_{13}fC_{14}G_{15}$ $fC_{16}fC_{17}G_{18}$ $fU_{19}A_{20}G_{21}$ $A_{22}A_{23}A_{24}$ $A_{25}G_{26}fC_{27}$ $A_{28}fU_{29}G_{30}$ $fU_{31}fC_{32}A_{33}$ $A_{34}A_{35}G_{36}$ $fC_{37}fC_{38}G_{39}$ $G_{40}A_{41}A_{42}$ $fC_{43}fC_{44}X_{45}$ $X_{46}X_{47}fC_{48}$-3', wherein $X_1$, $X_2$, $X_5$, $X_6$ and $X_{45}$ are either absent or G, $X_3$ and $X_7$ are either absent or A, $X_4$ and $X_{47}$ are either absent or fC and $X_8$, $X_9$ and $X_{46}$ are either absent or fU.

The skilled person will be aware that several of said nucleotide positions 1 to 48 may be absent, therefore, nucleotide sequences with less than 48 nucleotides are within the scope of the invention.

Figure 13:
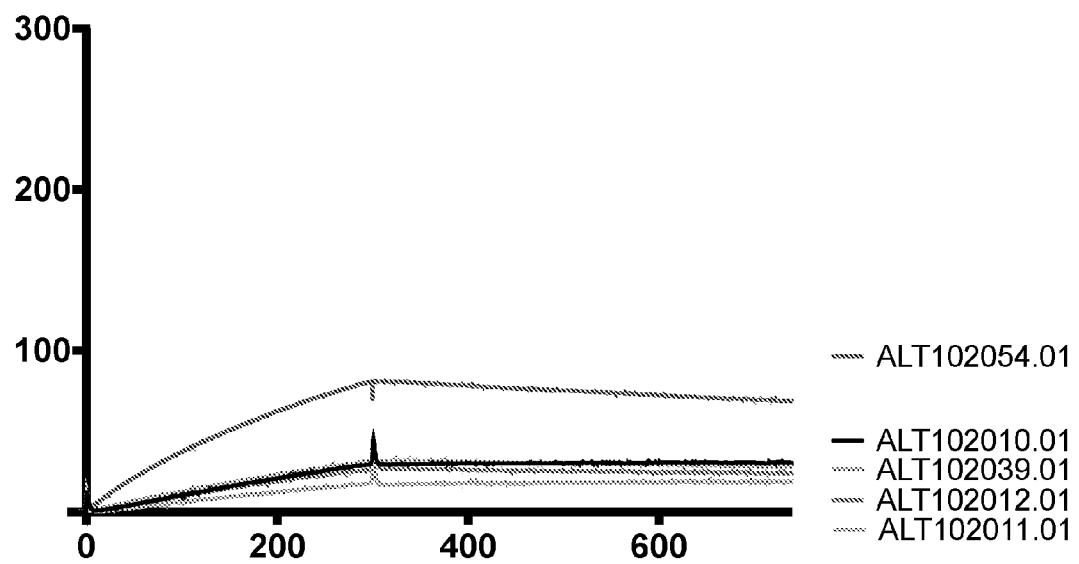

In one embodiment, at least 3 (such as 3) of $X_1$, $X_2$, $X_3$, $X_4$, $X_5$, $X_6$, $X_7$, $X_8$, $X_9$, $X_{45}$, $X_{46}$ and $X_{47}$ are absent. For example, in one embodiment $X_1$, $X_2$ and $X_3$ are each absent, $X_5$, $X_6$ and $X_{45}$ are G, $X_7$ is A, $X_4$ and $X_{47}$ are fC and $X_8$, $X_9$ and $X_{46}$ are fU. Thus, in a further embodiment, the ribonucleic acid molecule has a nucleotide sequence selected from:
5'-fCGG AfUfU fUAA fUfCG fCfCG fUAG AAA AGfC AfUG fUfCA AAG fCfCG GAA fCfCG fUfCfC-3' (ALT102010.01) (SEQ ID NO: 3). SPR data is provided herein which demonstrates that this aptamer exhibited medium binding (i.e. a reduced Rmax) to the EGFR recombinant protein (see FIG. 13, second trace from top).

In an alternative embodiment, $X_4$, $X_5$ and $X_6$ are each absent, $X_1$, $X_2$ and $X_{45}$ are G, $X_3$ and $X_7$ are A, $X_{47}$ is fC and $X_8$, $X_9$ and $X_{46}$ are fU. Thus, in a further embodiment, the ribonucleic acid molecule has a nucleotide sequence selected from:
5'-GGA AfUfU fUAA fUfCG fCfCG fUAG AAA AGfC AfUG fUfCA AAG fCfCG GAA fCfCG fUfCfC-3' (ALT102039.01) (SEQ ID NO: 4). SPR data is provided herein which demonstrates that this aptamer exhibited medium binding (i.e. a reduced Rmax) to the EGFR recombinant protein (see FIG. 13, third trace from top).

In one embodiment, at least 6 (such as 6) of $X_1$, $X_2$, $X_3$, $X_4$, $X_5$, $X_6$, $X_7$, $X_8$, $X_9$, $X_{45}$, $X_{46}$ and $X_{47}$ are absent. For example, in one embodiment, $X_1$, $X_2$, $X_3$, $X_4$, $X_5$ and $X_6$ are each absent, $X_{45}$ is G, $X_7$ is A, $X_{47}$ is fC and $X_8$, $X_9$ and $X_{46}$ are fU. Thus, in a further embodiment, the ribonucleic acid molecule has a nucleotide sequence selected from:
5'-AfUfU fUAA fUfCG fCfCG fUAG AAA AGfC AfUG fUfCA AAG fCfCG GAA fCfCG fUfCfC-3' (ALT102011.01) (SEQ ID NO: 5). SPR data is provided herein which demonstrates that this aptamer exhibited medium binding (i.e. a reduced Rmax) to the EGFR recombinant protein (see FIG. 13, lowest trace).

Figure 15:
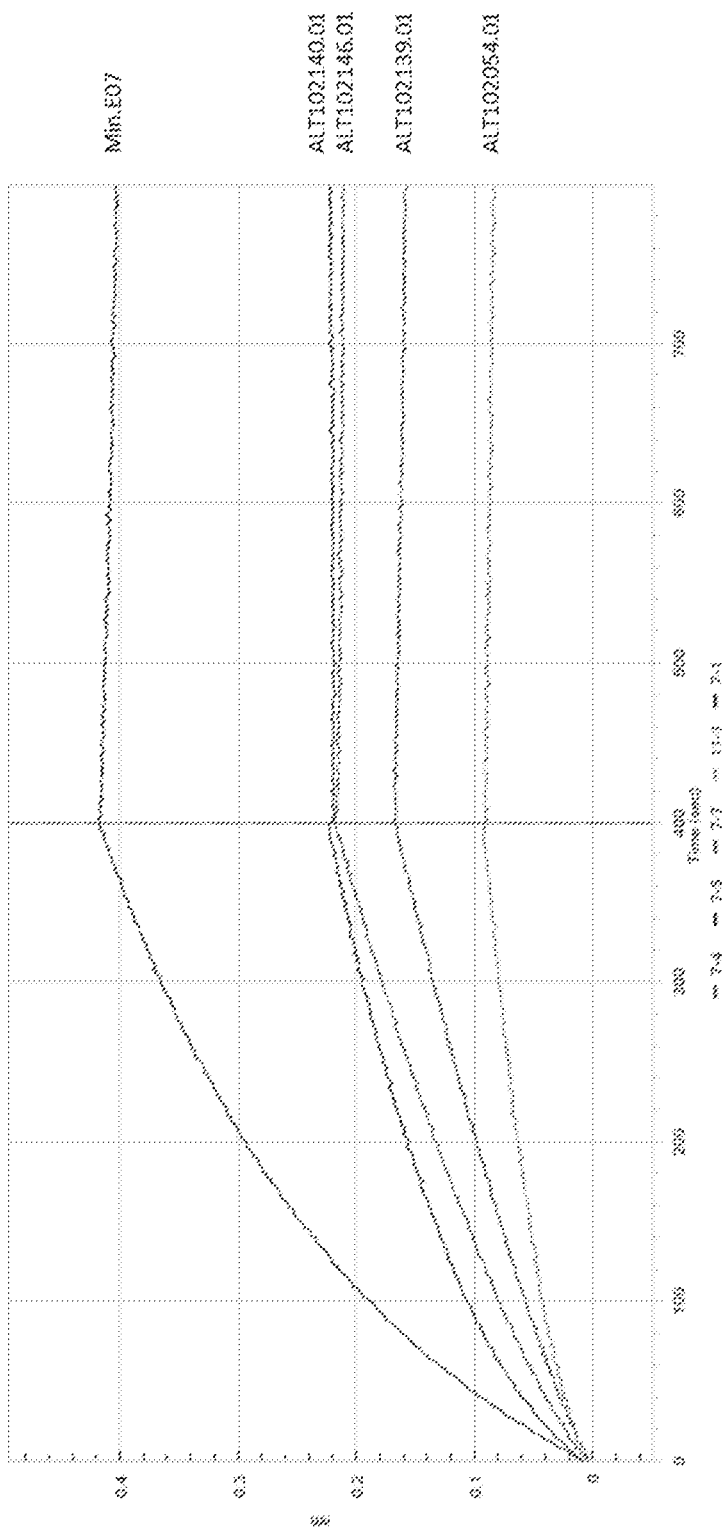
Figure 16:
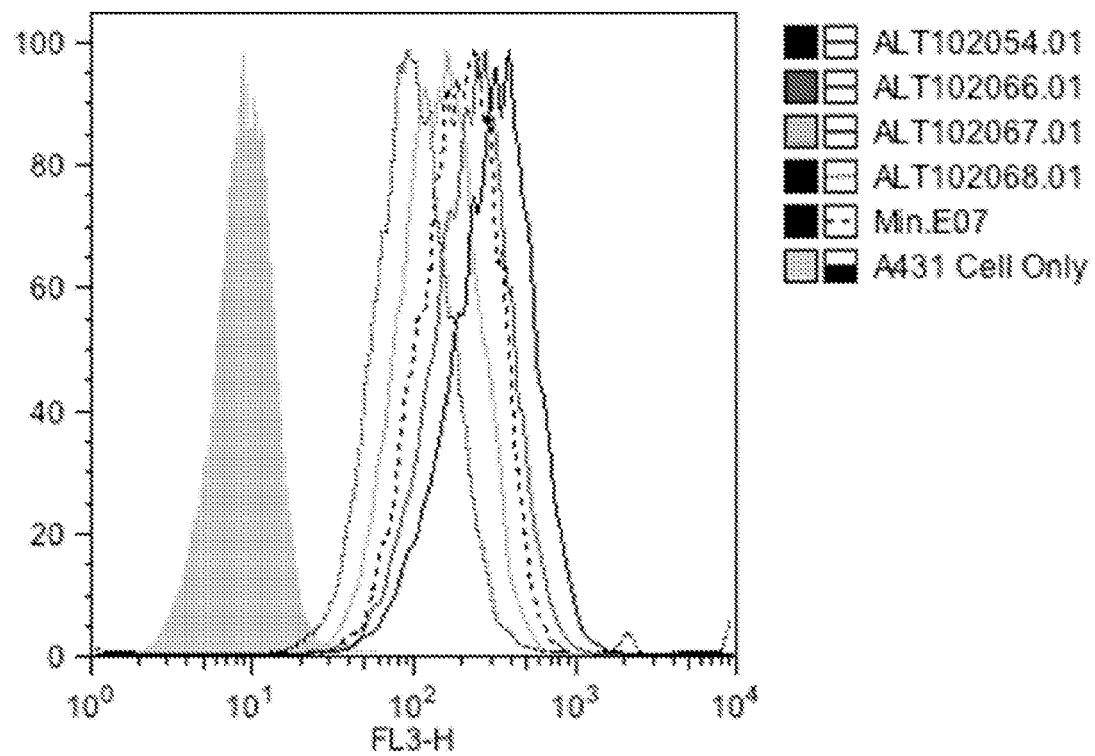
FIGS. 16 to 19 describe the results of the Flow Cytometry Assay analysis with selected aptamers of the invention.
Figure 19:
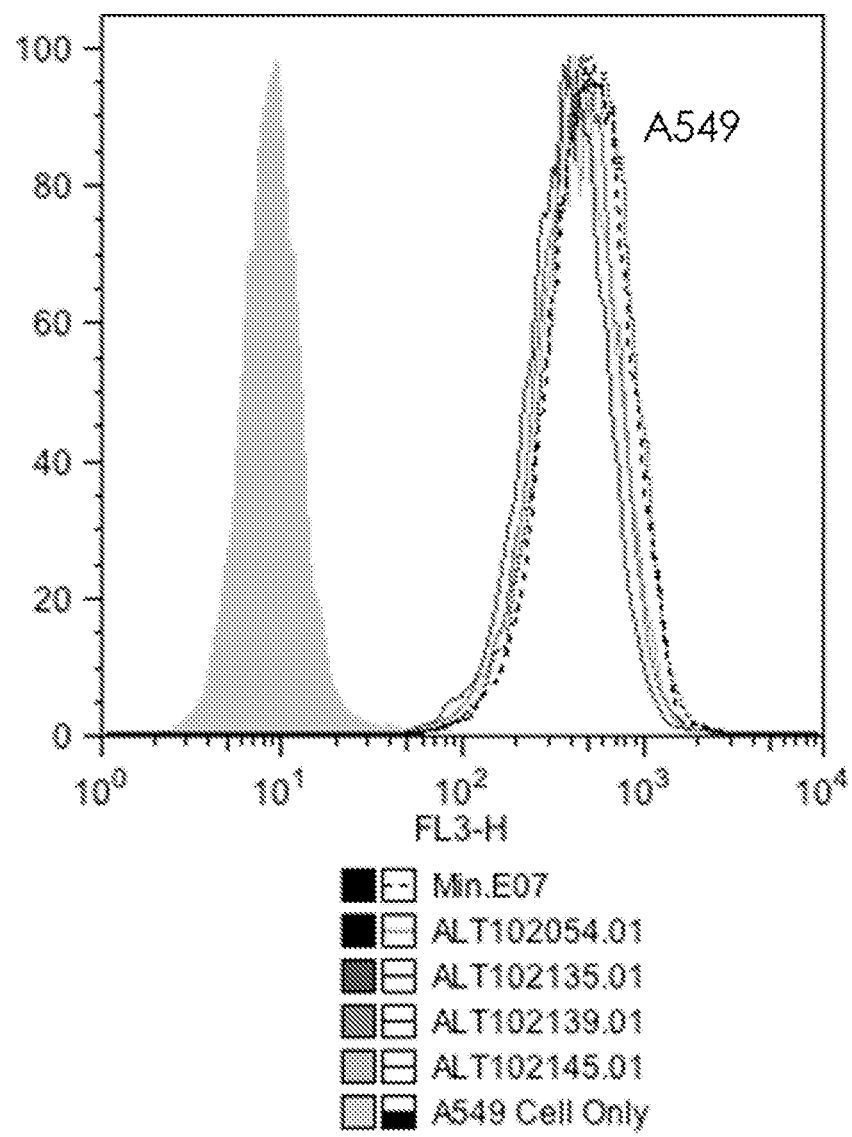

In an alternative embodiment, $X_2$, $X_3$, $X_4$, $X_{45}$, $X_{46}$ and $X_{47}$ are each absent, $X_1$, $X_5$ and $X_6$ are G, $X_7$ is A and $X_8$ and $X_9$ are fU. Thus, in a further embodiment, the ribonucleic acid molecule has a nucleotide sequence selected from:
5'-GGG AfUfU fUAA fUfCG fCfCG fUAG AAA AGfC AfUG fUfCA AAG fCfCG GAA fCfCfC-3' (ALT102054.01) (SEQ ID NO: 6). SPR data is provided herein which demonstrates that this aptamer bound to the EGFR recombinant protein (see FIG. 13, highest trace and FIG. 15, lowest trace) and FACS data is also provided which demonstrates that this aptamer exhibited high binding to two EGFR cell types (see FIG. 16 for binding to A431 cells and FIG. 19 for binding to A549 cells).

In one embodiment, at least 9 (such as 9) of $X_1$, $X_2$, $X_3$, $X_4$, $X_5$, $X_6$, $X_7$, $X_8$, $X_9$, $X_{45}$, $X_{46}$ and $X_{47}$ are absent. For example, in one embodiment, $X_1$, $X_2$, $X_3$, $X_4$, $X_5$, $X_6$, $X_7$, $X_8$ and $X_9$ are each absent, $X_{45}$ is G, $X_{47}$ is fC and $X_{46}$ is fU. Thus, in a further embodiment, the ribonucleic acid molecule has a nucleotide sequence selected from:

5'-fUAA fUfCG fCfCG fUAG AAA AGfC AfUG fUfCA AAG fCfCG GAA fCfCrG fUfCfC-3' (ALT102012.01) (SEQ ID NO: 7). SPR data is provided herein which demonstrates that this aptamer exhibited medium binding (i.e. a reduced Rmax) to the EGFR recombinant protein (see FIG. 13, fourth trace from top).

In one embodiment, $X_1$, $X_2$, $X_5$, $X_6$ and $X_{45}$ are G, $X_3$ and $X_7$ are A, $X_4$ and $X_{47}$ are C and $X_8$, $X_9$ and $X_{46}$ are U. Thus, in a further embodiment, the ribonucleic acid molecule has a nucleotide sequence selected from:

(SEQ ID NO: 8)
5'-G₁G₂A₃ C₄G₅G₆ A₇U₈U₉ U₁₀A₁₁A₁₂ U₁₃C₁₄G₁₅ C₁₆C₁₇G₁₈
U₁₉A₂₀G₂₁ A₂₂A₂₃A₂₄ A₂₅G₂₆C₂₇ A₂₈U₂₉G₃₀ U₃₁C₃₂A₃₃ A₃₄A₃₅G₃₆
C₃₇C₃₈G₃₉ G₄₀A₄₁A₄₂ C₄₃C₄₄G₄₅ U₄₆C₄₇C₄₈-3'.

In one embodiment, each of the 2'-OH groups of the C and U nucleotides within SEQ ID NO: 8 are modified to a 2'-F group. Thus, in a further embodiment, the ribonucleic acid molecule has a nucleotide sequence selected from:

(SEQ ID NO: 9)
5'-G₁G₂A₃ fC₄G₅G₆ A₇fU₈fU₉ fU₁₀A₁₁A₁₂ fU₁₃fC₁₄G₁₅
fC₁₆fC₁₇G₁₈ fU₁₉A₂₀G₂₁ A₂₂A₂₃A₂₄ A₂₅G₂₆fC₂₇ A₂₈fU₂₉G₃₀
fU₃₁fC₃₂A₃₃ A₃₄A₃₅G₃₆ fC₃₇fC₃₈G₃₉ G₄₀A₄₁A₄₂ fC₄₃fC₄₄G₄₅
fU₄₆fC₄₇fC₄₈-3'.

It will be appreciated that the 2'-OMe substitution may be present at one or more or even each of positions 1 to 11, 14 to 16, 18 to 28, 30, 33 and 35 to 48.

Thus, in one embodiment the 2'-OMe substitution is present at nucleotide position 1 and comprises the following sequence:
5'-mGGA fCGG AfUfU fUAA fUfCG fCfCG fUAG AAA AGfC AfUG fUfCA AAG fCfCG GAA fCfCrG fUfCfC-3' (ALT102058.01) (SEQ ID NO: 10). SPR data is provided herein which demonstrates that this aptamer bound to the EGFR recombinant protein (see FIG. 1, sixth trace from top).

In an alternative or additional embodiment the 2'-OMe substitution is present at nucleotide position 2 and comprises the following sequence:
5'-GmGA fCGG AfUfU fUAA fUfCG fCfCG fUAG AAA AGfC AfUG fUfCA AAG fCfCG GAA fCfCG fUfCfC-3' (ALT102059.01) (SEQ ID NO: 11). SPR data is provided herein which demonstrates that this aptamer bound to the EGFR recombinant protein (see FIG. 1, fifth trace from top).

In an alternative or additional embodiment the 2'-OMe substitution is present at nucleotide position 3 and comprises the following sequence:
5'-GGmA fCGG AfUfU fUAA fUfCG fCfCG fUAG AAA AGfC AfUG fUfCA AAG fCfCG GAA fCfCrG fUfCfC-3' (ALT102060.01) (SEQ ID NO: 12). SPR data is provided herein which demonstrates that this aptamer bound to the EGFR recombinant protein (see FIG. 1, highest trace).

In an alternative or additional embodiment the 2'-OMe substitution is present at nucleotide position 4 and comprises the following sequence:

5'-GGA mCGG AfUfU fUAA fUfCG fCfCG fUAG AAA AGfC AfUG fUfCA AAG fCfCG GAA fCfCG fUfCfC-3' (ALT102061.01) (SEQ ID NO: 13). SPR data is provided herein which demonstrates that this aptamer bound to the EGFR recombinant protein (see FIG. 1, fourth trace from top).

In an alternative or additional embodiment the 2'-OMe substitution is present at nucleotide position 5 and comprises the following sequence:
5'-GGA fCmGG AfUfU fUAA fUfCG fCfCG fUAG AAA AGfC AfUG fUfCA AAG fCfCG GAA fCfCG fUfCfC-3' (ALT102062.01) (SEQ ID NO: 14). SPR data is provided herein which demonstrates that this aptamer bound to the EGFR recombinant protein (see FIG. 1, second trace from top).

In an alternative or additional embodiment the 2'-OMe substitution is present at nucleotide position 6 and comprises the following sequence:
5'-GGA fCGmG AfUfU fUAA fUfCG fCfCG fUAG AAA AGfC AfUG fUfCA AAG fCfCG GAA fCfCG fUfCfC-3' (ALT102063.01) (SEQ ID NO: 15). SPR data is provided herein which demonstrates that this aptamer bound to the EGFR recombinant protein (see FIG. 1, lowest trace).

Figure 2:
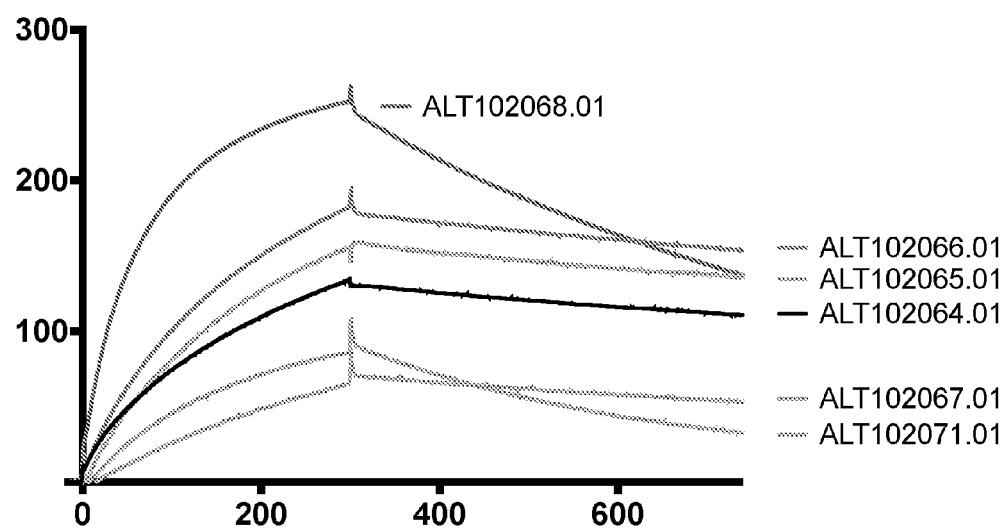

In an alternative or additional embodiment the 2'-OMe substitution is present at nucleotide position 7 and comprises the following sequence:
5'-GGA fCGG mAfUfU fUAA fUfCG fCfCG fUAG AAA AGfC AfUG fUfCA AAG fCfCG GAA fCfCG fUfCfC-3' (ALT102064.01) (SEQ ID NO: 16). SPR data is provided herein which demonstrates that this aptamer bound to the EGFR recombinant protein (see FIG. 2, fourth trace from top).

In an alternative or additional embodiment the 2'-OMe substitution is present at nucleotide position 8 and comprises the following sequence:
5'-GGA fCGG AmUfU fUAA fUfCG fCfCG fUAG AAA AGfC AfUG fUfCA AAG fCfCG GAA fCfCG fUfCfC-3' (ALT102065.01) (SEQ ID NO: 17). SPR data is provided herein which demonstrates that this aptamer bound to the EGFR recombinant protein (see FIG. 2, third trace from top).

In an alternative or additional embodiment the 2'-OMe substitution is present at nucleotide position 9 and comprises the following sequence:
5'-GGA fCGG AfUmU fUAA fUfCG fCfCG fUAG AAA AGfC AfUG fUfCA AAG fCfCG GAA fCfCG fUfCfC-3' (ALT102066.01) (SEQ ID NO: 18). SPR data is provided herein which demonstrates that this aptamer bound to the EGFR recombinant protein (see FIG. 2, second trace from top) and FACS data is also provided which demonstrates that this aptamer bound to EGFR cells (see FIG. 16 for binding to A431 cells).

In an alternative or additional embodiment the 2'-OMe substitution is present at nucleotide position 10 and comprises the following sequence:
5'-GGA fCGG AfUfU mUAA fUfCG fCfCG fUAG AAA AGfC AfUG fUfCA AAG fCfCG GAA fCfCG fUfCfC-3' (ALT102067.01) (SEQ ID NO: 19). SPR data is provided herein which demonstrates that this aptamer exhibited medium binding (i.e. a low Rmax) to the EGFR recombinant protein (see FIG. 2, fifth trace from top) and FACS data is also provided which demonstrates that this aptamer exhibited medium binding to EGFR cells (see FIG. 16 for binding to A431 cells).

In an alternative or additional embodiment the 2'-OMe substitution is present at nucleotide position 11 and comprises the following sequence:

5'-GGA fCGG AfUfU fUmAA fUfCG fCfCG fUAG AAA AGfC AfUG fUfCA AAG fCfCG GAA fCfCG fUfCfC-3' (ALT102068.01) (SEQ ID NO: 20). SPR data is provided herein which demonstrates that this aptamer exhibited medium binding (i.e. a faster "off" or disassociation) to the EGFR recombinant protein (see FIG. 2, highest trace) and FACS data is also provided which demonstrates that this aptamer exhibited medium binding to EGFR cells (see FIG. 16 for binding to A431 cells).

In an alternative or additional embodiment the 2'-OMe substitution is present at nucleotide position 14 and comprises the following sequence:
5'-GGA fCGG AfUfU fUAA fUmCG fCfCG fUAG AAA AGfC AfUG fUfCA AAG fCfCG GAA fCfCG fUfCfC-3' (ALT102071.01) (SEQ ID NO: 21). SPR data is provided herein which demonstrates that this aptamer exhibited medium binding (i.e. a faster "off" or disassociation) to the EGFR recombinant protein (see FIG. 2, lowest trace).

Figure 3:
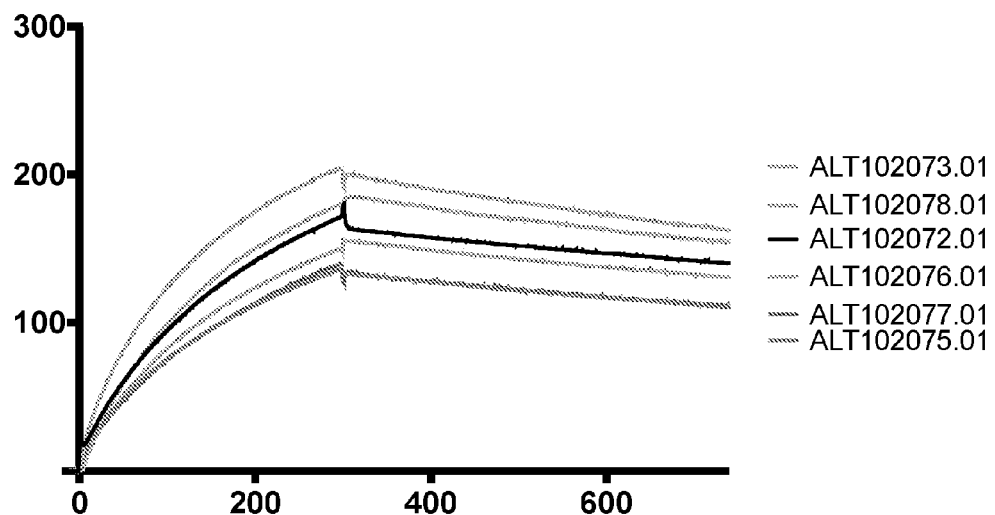

In an alternative or additional embodiment the 2'-OMe substitution is present at nucleotide position 15 and comprises the following sequence:
5'-GGA fCGG AfUfU fUAA fUfCmG fCfCG fUAG AAA AGfC AfUG fUfCA AAG fCfCG GAA fCfCG fUfCfC-3' (ALT102072.01) (SEQ ID NO: 22). SPR data is provided herein which demonstrates that this aptamer bound to the EGFR recombinant protein (see FIG. 3, third trace from top).

In an alternative or additional embodiment the 2'-OMe substitution is present at nucleotide position 16 and comprises the following sequence:
5'-GGA fCGG AfUfU fUAA fUfCG mCfCG fUAG AAA AGfC AfUG fUfCA AAG fCfCG GAA fCfCG fUfCfC-3' (ALT102073.01) (SEQ ID NO: 23). SPR data is provided herein which demonstrates that this aptamer bound to the EGFR recombinant protein (see FIG. 3, highest trace).

In an alternative or additional embodiment the 2'-OMe substitution is present at nucleotide position 18 and comprises the following sequence:
5'-GGA fCGG AfUfU fUAA fUfCG fCfCmG fUAG AAA AGfC AfUG fUfCA AAG fCfCG GAA fCfCG fUfCfC-3' (ALT102075.01) (SEQ ID NO: 24). SPR data is provided herein which demonstrates that this aptamer bound to the EGFR recombinant protein (see FIG. 3, lowest trace).

In an alternative or additional embodiment the 2'-OMe substitution is present at nucleotide position 19 and comprises the following sequence:
5'-GGA fCGG AfUfU fUAA fUfCG fCfCG mUAG AAA AGfC AfUG fUfCA AAG fCfCG GAA fCfCG fUfCfC-3' (ALT102076.01) (SEQ ID NO: 25). SPR data is provided herein which demonstrates that this aptamer bound to the EGFR recombinant protein (see FIG. 3, fourth trace from top).

In an alternative or additional embodiment the 2'-OMe substitution is present at nucleotide position 20 and comprises the following sequence:
5'-GGA fCGG AfUfU fUAA fUfCG fCfCG fUmAG AAA AGfC AfUG fUfCA AAG fCfCG GAA fCfCG fUfCfC-3' (ALT102077.01) (SEQ ID NO: 26). SPR data is provided herein which demonstrates that this aptamer bound to the EGFR recombinant protein (see FIG. 3, fifth trace from top).

In an alternative or additional embodiment the 2'-OMe substitution is present at nucleotide position 21 and comprises the following sequence:
5'-GGA fCGG AfUfU fUAA fUfCG fCfCG fUAmG AAA AGfC AfUG fUfCA AAG fCfCG GAA fCfCG fUfCfC-3' (ALT102078.01) (SEQ ID NO: 27). SPR data is provided herein which demonstrates that this aptamer bound to the EGFR recombinant protein (see FIG. 3, second trace from top).

Figure 4:
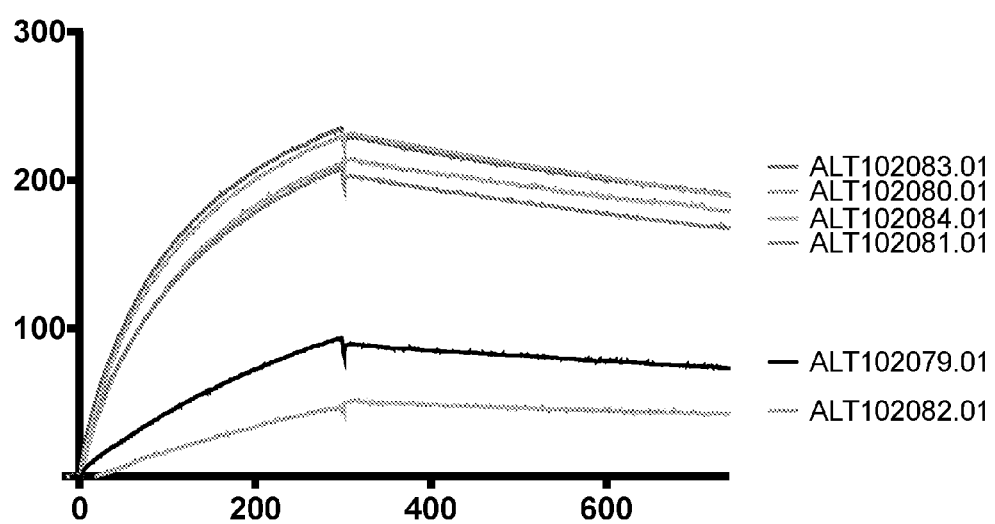

In an alternative or additional embodiment the 2'-OMe substitution is present at nucleotide position 22 and comprises the following sequence:
5'-GGA fCGG AfUfU fUAA fUfCG fCfCG fUAG mAAA AGfC AfUG fUfCA AAG fCfCG GAA fCfCG fUfCfC-3' (ALT102079.01) (SEQ ID NO: 28). SPR data is provided herein which demonstrates that this aptamer exhibited medium binding (i.e. a low Rmax) to the EGFR recombinant protein (see FIG. 4, fifth trace from top).

In an alternative or additional embodiment the 2'-OMe substitution is present at nucleotide position 23 and comprises the following sequence:
5'-GGA fCGG AfUfU fUAA fUfCG fCfCG fUAG AmAA AGfC AfUG fUfCA AAG fCfCG GAA fCfCG fUfCfC-3' (ALT102080.01) (SEQ ID NO: 29). SPR data is provided herein which demonstrates that this aptamer bound to the EGFR recombinant protein (see FIG. 4, second trace from top).

In an alternative or additional embodiment the 2'-OMe substitution is present at nucleotide position 24 and comprises the following sequence:
5'-GGA fCGG AfUfU fUAA fUfCG fCfCG fUAG AAmA AGfC AfUG fUfCA AAG fCfCG GAA fCfCrG fUfCfC-3' (ALT102081.01) (SEQ ID NO: 30). SPR data is provided herein which demonstrates that this aptamer bound to the EGFR recombinant protein (see FIG. 4, fourth trace from top).

In an alternative or additional embodiment the 2'-OMe substitution is present at nucleotide position 25 and comprises the following sequence:
5'-GGA fCGG AfUfU fUAA fUfCG fCfCG fUAG AAA mAGfC AfUG fUfCA AAG fCfCG GAA fCfCG fUfCfC-3' (ALT102082.01) (SEQ ID NO: 31). SPR data is provided herein which demonstrates that this aptamer exhibited medium binding (i.e. a low Rmax) to the EGFR recombinant protein (see FIG. 4, lowest trace).

In an alternative or additional embodiment the 2'-OMe substitution is present at nucleotide position 26 and comprises the following sequence:
5'-GGA fCGG AfUfU fUAA fUfCG fCfCG fUAG AAA AmGfC AfUG fUfCA AAG fCfCG GAA fCfCG fUfCfC-3' (ALT102083.01) (SEQ ID NO: 32). SPR data is provided herein which demonstrates that this aptamer bound to the EGFR recombinant protein (see FIG. 4, highest trace).

In an alternative or additional embodiment the 2'-OMe substitution is present at nucleotide position 27 and comprises the following sequence:
5'-GGA fCGG AfUfU fUAA fUfCG fCfCG fUAG AAA AGmC AfUG fUfCA AAG fCfCG GAA fCfCG fUfCfC-3' (ALT102084.01) (SEQ ID NO: 33). SPR data is provided herein which demonstrates that this aptamer bound to the EGFR recombinant protein (see FIG. 4, third trace from top).

Figure 5:
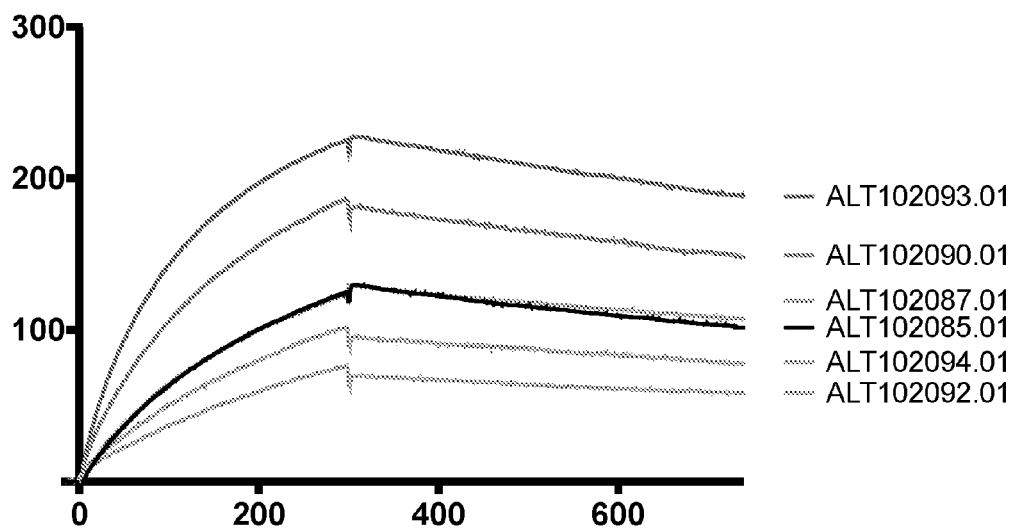

In an alternative or additional embodiment the 2'-OMe substitution is present at nucleotide position 28 and comprises the following sequence:
5'-GGA fCGG AfUfU fUAA fUfCG fCfCG fUAG AAA AGfC mAfUG fUfCA AAG fCfCG GAA fCfCG fUfCfC-3' (ALT102085.01) (SEQ ID NO: 34). SPR data is provided herein which demonstrates that this aptamer bound to the EGFR recombinant protein (see FIG. 5, fourth trace from top).

In an alternative or additional embodiment the 2'-OMe substitution is present at nucleotide position 30 and comprises the following sequence:
5'-GGA fCGG AfUfU fUAA fUfCG fCfCG fUAG AAA AGfC AfUmG fUfCA AAG fCfCG GAA fCfCG fUfCfC-3' (ALT102087.01) (SEQ ID NO: 35). SPR data is provided herein which demonstrates that this aptamer bound to the EGFR recombinant protein (see FIG. 5, third trace from top).

In an alternative or additional embodiment the 2'-OMe substitution is present at nucleotide position 33 and comprises the following sequence:
5'-GGA fCGG AfUfU fUAA fUfCG fCfCG fUAG AAA AGfC AfUG fUfCmA AAG fCfCG GAA fCfCG fUfCfC-3' (ALT102090.01) (SEQ ID NO: 36). SPR data is provided herein which demonstrates that this aptamer bound to the EGFR recombinant protein (see FIG. 5, second trace from top).

In an alternative or additional embodiment the 2'-OMe substitution is present at nucleotide position 35 and comprises the following sequence:
5'-GGA fCGG AfUfU fUAA fUfCG fCfCG fUAG AAA AGfC AfUG fUfCA AmAG fCfCG GAA fCfCG fUfCfC-3' (ALT102092.01) (SEQ ID NO: 37). SPR data is provided herein which demonstrates that this aptamer exhibited medium binding (i.e. a low Rmax) to the EGFR recombinant protein (see FIG. 5, lowest trace).

In an alternative or additional embodiment the 2'-OMe substitution is present at nucleotide position 36 and comprises the following sequence:
5'-GGA fCGG AfUfU fUAA fUfCG fCfCG fUAG AAA AGfC AfUG fUfCA AAmG fCfCG GAA fCfCG fUfCfC-3' (ALT102093.01) (SEQ ID NO: 38). SPR data is provided herein which demonstrates that this aptamer bound to the EGFR recombinant protein (see FIG. 5, highest trace).

In an alternative or additional embodiment the 2'-OMe substitution is present at nucleotide position 37 and comprises the following sequence:
5'-GGA fCGG AfUfU fUAA fUfCG fCfCG fUAG AAA AGfC AfUG fUfCA AAG mCfCG GAA fCfCG fUfCfC-3' (ALT102094.01) (SEQ ID NO: 39). SPR data is provided herein which demonstrates that this aptamer bound to the EGFR recombinant protein (see FIG. 5, fifth trace from top).

Figure 6:
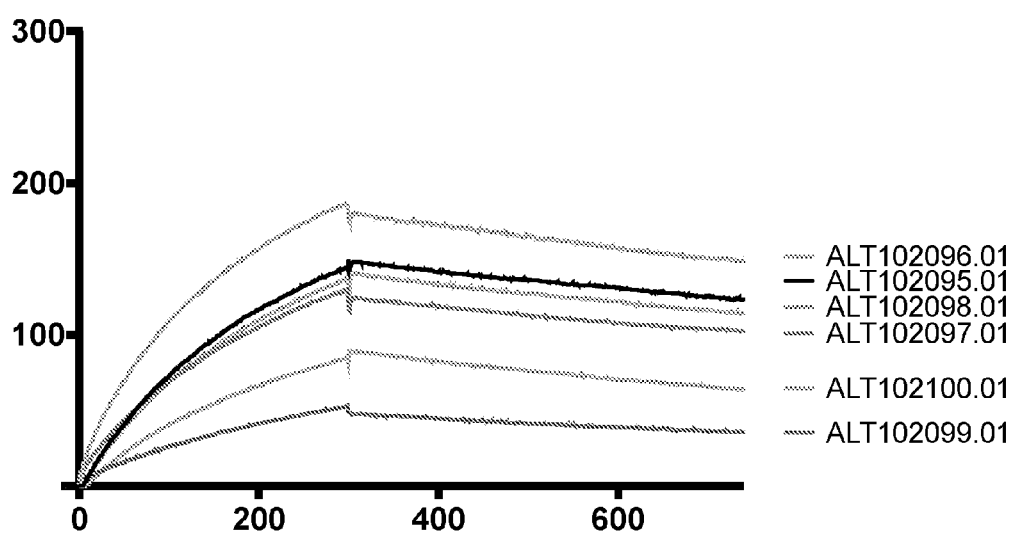

In an alternative or additional embodiment the 2'-OMe substitution is present at nucleotide position 38 and comprises the following sequence:
5'-GGA fCGG AfUfU fUAA fUfCG fCfCG fUAG AAA AGfC AfUG fUfCA AAG fCmCG GAA fCfCG fUfCfC-3' (ALT102095.01) (SEQ ID NO: 40). SPR data is provided herein which demonstrates that this aptamer bound to the EGFR recombinant protein (see FIG. 6, second trace from top).

In an alternative or additional embodiment the 2'-OMe substitution is present at nucleotide position 39 and comprises the following sequence:
5'-GGA fCGG AfUfU fUAA fUfCG fCfCG fUAG AAA AGfC AfUG fUfCA AAG fCfCmG GAA fCfCG fUfCfC-3' (ALT102096.01) (SEQ ID NO: 41). SPR data is provided herein which demonstrates that this aptamer bound to the EGFR recombinant protein (see FIG. 6, highest trace).

In an alternative or additional embodiment the 2'-OMe substitution is present at nucleotide position 40 and comprises the following sequence:
5'-GGA fCGG AfUfU fUAA fUfCG fCfCG fUAG AAA AGfC AfUG fUfCA AAG fCfCG mGAA fCfCG fUfCfC-3' (ALT102097.01) (SEQ ID NO: 42). SPR data is provided herein which demonstrates that this aptamer bound to the EGFR recombinant protein (see FIG. 6, fourth trace from top).

In an alternative or additional embodiment the 2'-OMe substitution is present at nucleotide position 41 and comprises the following sequence:
5'-GGA fCGG AfUfU fUAA fUfCG fCfCG fUAG AAA AGfC AfUG fUfCA AAG fCfCG GmAA fCfCG fUfCfC-3' (ALT102098.01) (SEQ ID NO: 43). SPR data is provided herein which demonstrates that this aptamer bound to the EGFR recombinant protein (see FIG. 6, third trace from top).

In an alternative or additional embodiment the 2'-OMe substitution is present at nucleotide position 42 and comprises the following sequence:
5'-GGA fCGG AfUfU fUAA fUfCG fCfCG fUAG AAA AGfC AfUG fUfCA AAG fCfCG GAmA fCfCG fUfCfC-3' (ALT102099.01) (SEQ ID NO: 44). SPR data is provided herein which demonstrates that this aptamer exhibited medium binding (i.e. a low Rmax) to the EGFR recombinant protein (see FIG. 6, lowest trace).

In an alternative or additional embodiment the 2'-OMe substitution is present at nucleotide position 43 and comprises the following sequence:
5'-GGA fCGG AfUfU fUAA fUfCG fCfCG fUAG AAA AGfC AfUG fUfCA AAG fCfCG GAA mCfCG fUfCfC-3' (ALT102100.01) (SEQ ID NO: 45). SPR data is provided herein which demonstrates that this aptamer exhibited medium binding (i.e. a low Rmax) to the EGFR recombinant protein (see FIG. 6, fifth trace from top).

Figure 7:
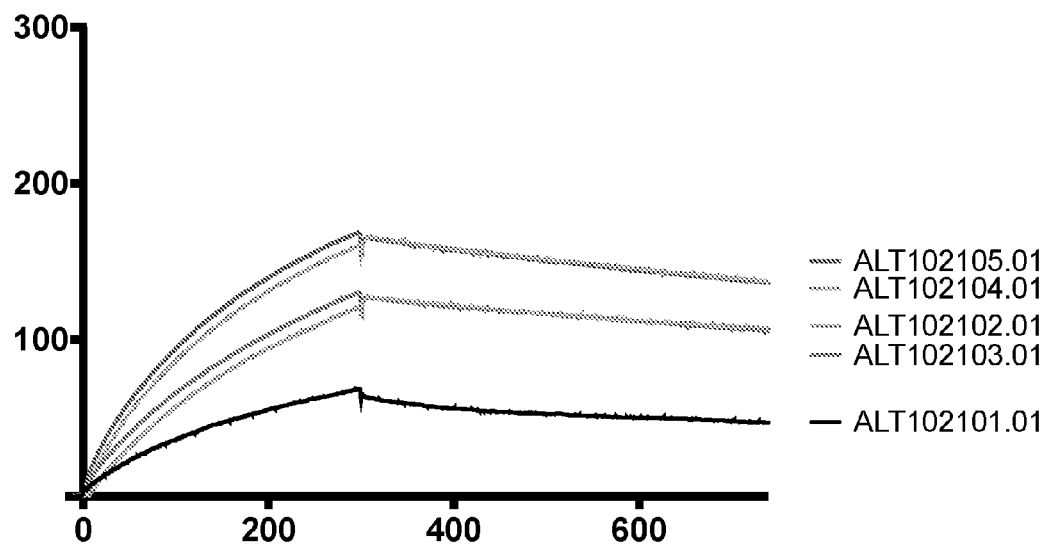

In an alternative or additional embodiment the 2'-OMe substitution is present at nucleotide position 44 and comprises the following sequence:
5'-GGA fCGG AfUfU fUAA fUfCG fCfCG fUAG AAA AGfC AfUG fUfCA AAG fCfCG GAA fCmCG fUfCfC-3' (ALT102101.01) (SEQ ID NO: 46). SPR data is provided herein which demonstrates that this aptamer exhibited medium binding (i.e. a low Rmax) to the EGFR recombinant protein (see FIG. 7, lowest trace).

In an alternative or additional embodiment the 2'-OMe substitution is present at nucleotide position 45 and comprises the following sequence:
5'-GGA fCGG AfUfU fUAA fUfCG fCfCG fUAG AAA AGfC AfUG fUfCA AAG fCfCG GAA fCfCmG fUfCfC-3' (ALT102102.01) (SEQ ID NO: 47). SPR data is provided herein which demonstrates that this aptamer bound to the EGFR recombinant protein (see FIG. 7, third trace from top).

In an alternative or additional embodiment the 2'-OMe substitution is present at nucleotide position 46 and comprises the following sequence:
5'-GGA fCGG AfUfU fUAA fUfCG fCfCG fUAG AAA AGfC AfUG fUfCA AAG fCfCG GArA fCfCG mUfCfC-3' (ALT102103.01) (SEQ ID NO: 48). SPR data is provided herein which demonstrates that this aptamer bound to the EGFR recombinant protein (see FIG. 7, fourth trace from top).

In an alternative or additional embodiment the 2'-OMe substitution is present at nucleotide position 47 and comprises the following sequence:
5'-GGA fCGG AfUfU fUAA fUfCG fCfCG fUAG AAA AGfC AfUG fUfCA AAG fCfCG GAA fCfCG fUmCfC-3' (ALT102104.01) (SEQ ID NO: 49). SPR data is provided herein which demonstrates that this aptamer bound to the EGFR recombinant protein (see FIG. 7, second trace from top).

In an alternative or additional embodiment the 2'-OMe substitution is present at nucleotide position 48 and comprises the following sequence:
5'-GGA fCGG AfUfU fUAA fUfCG fCfCG fUAG AAA AGfC AfUG fUfCA AAG fCfCG GAA fCfCG fUfCmC-3' (ALT102105.01) (SEQ ID NO: 50). SPR data is provided herein which demonstrates that this aptamer bound to the EGFR recombinant protein (see FIG. 7, highest trace).

In a further embodiment, the 2'-OMe substitution is present at one or more or even each of positions 1 to 9, 15 to 16, 18 to 21, 23-24, 26-28, 30, 33, 36-41 and 45 to 48 (i.e. the sequences set out hereinbefore). These positions provide the advantage of demonstrating a good level of binding to the EGFR recombinant protein from the SPR data provided herein.

Figure 14:
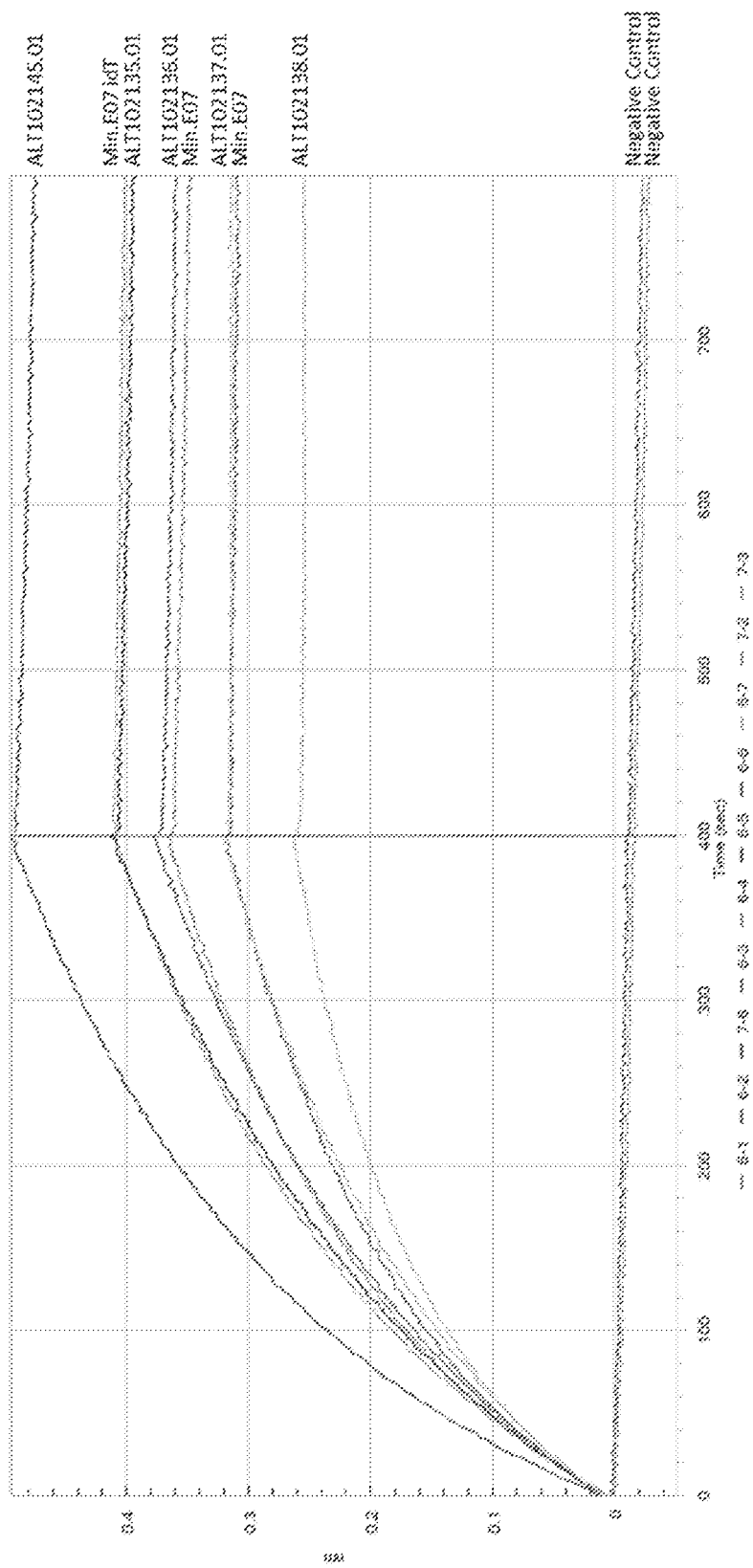
Figure 18:
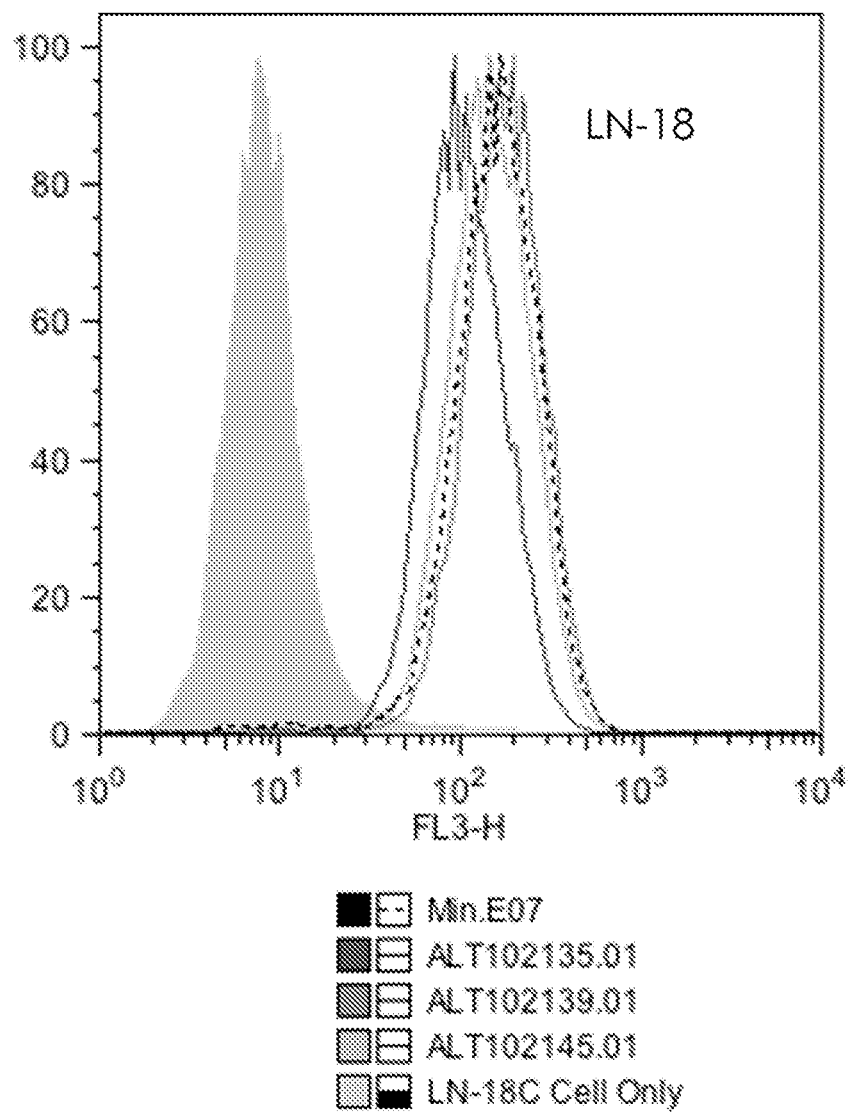

In an alternative embodiment, the 2'-OMe substitution is present at one or more or even each of positions 1 to 3, 5 to 7, 15, 18, 20 to 21, 23 to 24, 26, 28, 30, 33, 36, 39 to 41 and 45 (i.e. the sequences set out hereinbefore). In a further embodiment, the 2'-OMe substitution is present at each of positions 1 to 3, 5 to 7, 15, 18, 20 to 21, 23 to 24, 26, 28, 30, 33, 36, 39 to 41 and 45, for example:
5'-mGmGmA fCmGmG mAfUfU fUAA fUfCmG fCfCmG fUmAmG AmAmA AmGfC mAfUmG fUfCmA AAmG fCfCmG mGmAA fCfCmG fUfCfC-3' (ALT102135.01) (SEQ ID NO: 51). The aptamer of this embodiment exhibited both a good level of binding to the EGFR recombinant protein from the SPR data provided herein (see FIG. 14, third trace from top) and a good level of binding to two EGFR cell types from the FACS data provided herein (see FIG. 18 for binding to LN-18 cells and FIG. 19 for binding to A549 cells).

In a yet further embodiment, the 2'-OMe substitution is present at position 9 (i.e. the sequence of ALT102066.01 (SEQ ID NO: 18)). This position provides the advantage of demonstrating both a good level of binding to the EGFR recombinant protein from the SPR data provided herein and a good level of binding to EGFR cells from the FACS data provided herein.

It will be appreciated that the 2'-F substitution may be present at one or more or even each of positions 1 to 3, 5 to 7, 11 to 12, 15, 18, 20 to 26, 28, 30, 33, 36, 39 to 42 and 45.

Figure 8:
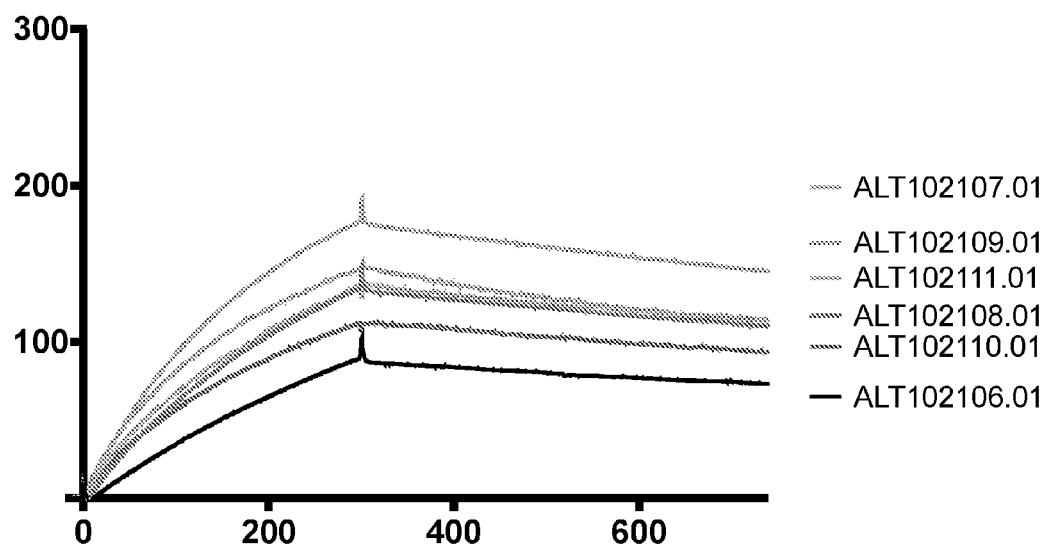

Thus, in one embodiment the 2'-F substitution is present at nucleotide position 1 and comprises the following sequence:
5'-fGGA fCGG AfUfU fUAA fUfCG fCfCG fUAG AAA AGfC AfUG fUfCA AAG fCfCG GAA fCfCG fUfCfC-3' (ALT102106.01) (SEQ ID NO: 52). SPR data is provided herein which demonstrates that this aptamer exhibited medium binding (i.e. a slightly lower Rmax) to the EGFR recombinant protein (see FIG. 8, lowest trace).

In an alternative or additional embodiment the 2'-F substitution is present at nucleotide position 2 and comprises the following sequence:
5'-GfGA fCGG AfUfU fUAA fUfCG fCfCG fUAG AAA AGfC AfUG fUfCA AAG fCfCG GAA fCfCG fUfCfC-3' (ALT102107.01) (SEQ ID NO: 53). SPR data is provided herein which demonstrates that this aptamer bound to the EGFR recombinant protein (see FIG. 8, highest trace).

In an alternative or additional embodiment the 2'-F substitution is present at nucleotide position 3 and comprises the following sequence:
5'-GGfA fCGG AfUfU fUAA fUfCG fCfCG fUAG AAA AGfC AfUG fUfCA AAG fCfCG GAA fCfCG fUfCfC-3' (ALT102108.01) (SEQ ID NO: 54). SPR data is provided herein which demonstrates that this aptamer bound to the EGFR recombinant protein (see FIG. 8, fourth trace from top).

In an alternative or additional embodiment the 2'-F substitution is present at nucleotide position 5 and comprises the following sequence:
5'-GGA fCfGG AfUfU fUAA fUfCG fCfCG fUAG AAA AGfC AfUG fUfCA AAG fCfCG GAA fCfCG fUfCfC-3' (ALT102109.01) (SEQ ID NO: 55). SPR data is provided herein which demonstrates that this aptamer bound to the EGFR recombinant protein (see FIG. 8, second trace from top).

In an alternative or additional embodiment the 2'-F substitution is present at nucleotide position 6 and comprises the following sequence:
5'-GGA fCGfG AfUfU fUAA fUfCG fCfCG fUAG AAA AGfC AfUG fUfCA AAG fCfCG GAA fCfCG fUfCfC-3' (ALT102110.01) (SEQ ID NO: 56). SPR data is provided herein which demonstrates that this aptamer bound to the EGFR recombinant protein (see FIG. 8, fifth trace from top).

In an alternative or additional embodiment the 2'-F substitution is present at nucleotide position 7 and comprises the following sequence:
5'-GGA fCGG fAfUfU fUAA fUfCG fCfCG fUAG AAA AGfC AfUG fUfCA AAG fCfCG GAA fCfCG fUfCfC-3' (ALT102111.01) (SEQ ID NO: 57). SPR data is provided herein which demonstrates that this aptamer bound to the EGFR recombinant protein (see FIG. 8, third trace from top).

Figure 9:
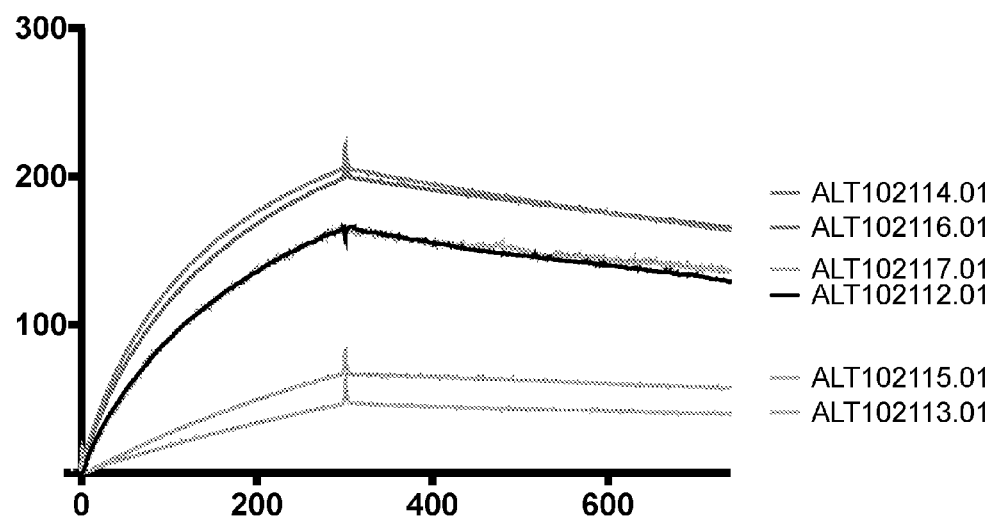

In an alternative or additional embodiment the 2'-F substitution is present at nucleotide position 11 and comprises the following sequence:
5'-GGA fCGG AfUfU fUAfAA fUfCG fCfCG fUAG AAA AGfC AfUG fUfCA AAG fCfCG GAA fCfCG fUfCfC-3' (ALT102112.01) (SEQ ID NO: 58). SPR data is provided herein which demonstrates that this aptamer bound to the EGFR recombinant protein (see FIG. 9, fourth trace from top).

In an alternative or additional embodiment the 2'-F substitution is present at nucleotide position 12 and comprises the following sequence:
5'-GGA fCGG AfUfU fUAfA fUfCG fCfCG fUAG AAA AGfC AfUG fUfCA AAG fCfCG GAA fCfCG fUfCfC-3' (ALT102113.01) (SEQ ID NO: 59). SPR data is provided herein which demonstrates that this aptamer exhibited medium binding (i.e. a low Rmax) to the EGFR recombinant protein (see FIG. 9, lowest trace).

In an alternative or additional embodiment the 2'-F substitution is present at nucleotide position 15 and comprises the following sequence:
5'-GGA fCGG AfUfU fUAA fUfCfG fCfCG fUAG AAA AGfC AfUG fUfCA AAG fCfCG GAA fCfCG fUfCfC-3' (ALT102114.01) (SEQ ID NO: 60). SPR data is provided herein which demonstrates that this aptamer bound to the EGFR recombinant protein (see FIG. 9, highest trace).

In an alternative or additional embodiment the 2'-F substitution is present at nucleotide position 18 and comprises the following sequence:
5'-GGA fCGG AfUfU fUAA fUfCG fCfCfG fUAG AAA AGfC AfUG fUfCA AAG fCfCG GAA fCfCG fUfCfC-3' (ALT102115.01) (SEQ ID NO: 61). SPR data is provided herein which demonstrates that this aptamer exhibited medium binding (i.e. a low Rmax) to the EGFR recombinant protein (see FIG. 9, fifth trace from top).

In an alternative or additional embodiment the 2'-F substitution is present at nucleotide position 20 and comprises the following sequence:

5'-GGA fCGG AfUfU fUAA fUfCG fCfCG fUfAG AAA AGfC AfUG fUfCA AAG fCfCG GAA fCfCG fUfCfC-3' (ALT102116.01) (SEQ ID NO: 62). SPR data is provided herein which demonstrates that this aptamer bound to the EGFR recombinant protein (see FIG. 9, second trace from top).

In an alternative or additional embodiment the 2'-F substitution is present at nucleotide position 21 and comprises the following sequence:
5'-GGA fCGG AfUfU fUAA fUfCG fCfCG fUAfG AAA AGfC AfUG fUfCA AAG fCfCG GAA fCfCG fUfCfC-3' (ALT102117.01) (SEQ ID NO: 63). SPR data is provided herein which demonstrates that this aptamer bound to the EGFR recombinant protein (see FIG. 9, third trace from top).

Figure 10:
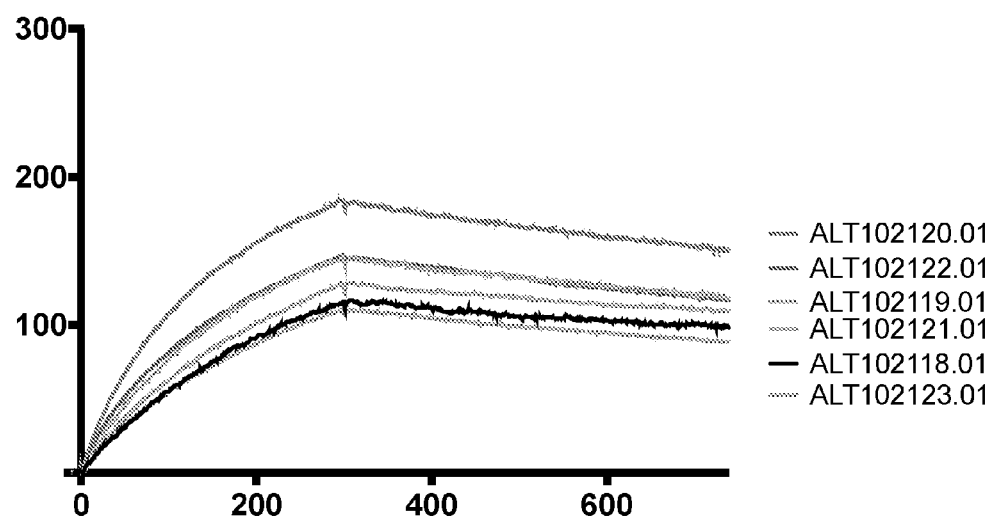

In an alternative or additional embodiment the 2'-F substitution is present at nucleotide position 22 and comprises the following sequence:
5'-GGA fCGG AfUfU fUAA fUfCG fCfCG fUAG fAAA AGfC AfUG fUfCA AAG fCfCG GAA fCfCG fUfCfC-3' (ALT102118.01) (SEQ ID NO: 64). SPR data is provided herein which demonstrates that this aptamer bound to the EGFR recombinant protein (see FIG. 10, fifth trace from top).

In an alternative or additional embodiment the 2'-F substitution is present at nucleotide position 23 and comprises the following sequence:
5'-GGA fCGG AfUfU fUAA fUfCG fCfCG fUAG AfAA AGfC AfUG fUfCA AAG fCfCG GAA fCfCG fUfCfC-3' (ALT102119.01) (SEQ ID NO: 65). SPR data is provided herein which demonstrates that this aptamer bound to the EGFR recombinant protein (see FIG. 10, third trace from top).

In an alternative or additional embodiment the 2'-F substitution is present at nucleotide position 24 and comprises the following sequence:
5'-GGA fCGG AfUfU fUAA fUfCG fCfCG fUAG AAfA AGfC AfUG fUfCA AAG fCfCG GAA fCfCG fUfCfC-3' (ALT102120.01) (SEQ ID NO: 66). SPR data is provided herein which demonstrates that this aptamer bound to the EGFR recombinant protein (see FIG. 10, highest trace).

In an alternative or additional embodiment the 2'-F substitution is present at nucleotide position 25 and comprises the following sequence:
5'-GGA fCGG AfUfU fUAA fUfCG fCfCG fUAG AAA fAGfC AfUG fUfCA AAG fCfCG GAA fCfCG fUfCfC-3' (ALT102121.01) (SEQ ID NO: 67). SPR data is provided herein which demonstrates that this aptamer bound to the EGFR recombinant protein (see FIG. 10, fourth trace from top).

In an alternative or additional embodiment the 2'-F substitution is present at nucleotide position 26 and comprises the following sequence:
5'-GGA fCGG AfUfU fUAA fUfCG fCfCG fUAG AAA AfGfC AfUG fUfCA AAG fCfCG GAA fCfCG fUfCfC-3' (ALT102122.01) (SEQ ID NO: 68). SPR data is provided herein which demonstrates that this aptamer bound to the EGFR recombinant protein (see FIG. 10, second trace from top).

In an alternative or additional embodiment the 2'-F substitution is present at nucleotide position 28 and comprises the following sequence:
5'-GGA fCGG AfUfU fUAA fUfCG fCfCG fUAG AAA AGfC fAfUG fUfCA AAG fCfCG GAA fCfCG fUfCfC-3' (ALT102123.01) (SEQ ID NO: 69). SPR data is provided herein which demonstrates that this aptamer bound to the EGFR recombinant protein (see FIG. 10, lowest trace).

Figure 11:
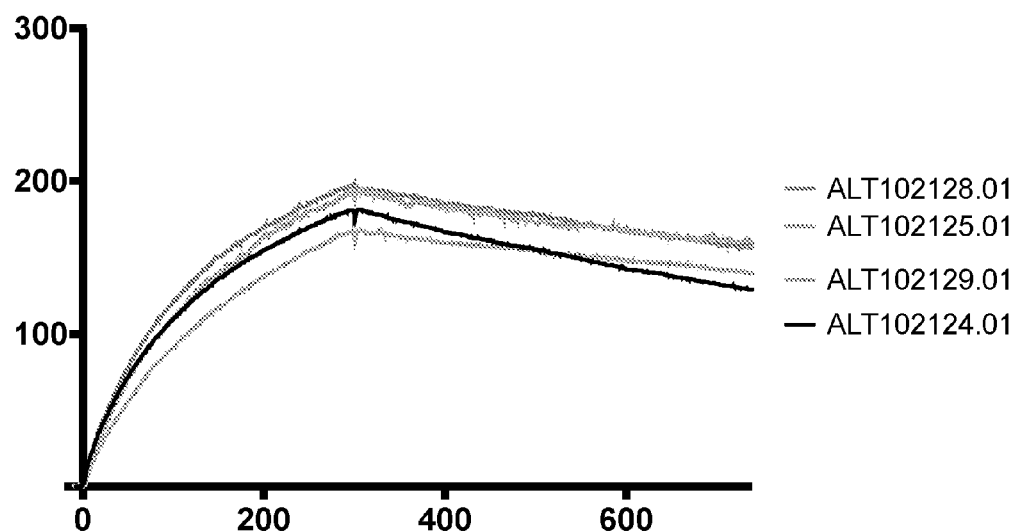

In an alternative or additional embodiment the 2'-F substitution is present at nucleotide position 30 and comprises the following sequence:
5'-GGA fCGG AfUfU fUAA fUfCG fCfCG fUAG AAA AGfC AfUfG fUfCA AAG fCfCG GAA fCfCG fUfCfC-3' (ALT102124.01) (SEQ ID NO: 70). SPR data is provided herein which demonstrates that this aptamer exhibited medium binding (i.e. a faster "off" or disassociation) to the EGFR recombinant protein (see FIG. 11, lowest trace).

In an alternative or additional embodiment the 2'-F substitution is present at nucleotide position 33 and comprises the following sequence:
5'-GGA fCGG AfUfU fUAA fUfCG fCfCG fUAG AAA AGfC AfUG fUfCfA AAG fCfCG GAA fCfCG fUfCfC-3' (ALT102125.01) (SEQ ID NO: 71). SPR data is provided herein which demonstrates that this aptamer bound to the EGFR recombinant protein (see FIG. 11, second trace from top).

In an alternative or additional embodiment the 2'-F substitution is present at nucleotide position 36 and comprises the following sequence:
5'-GGA fCGG AfUfU fUAA fUfCG fCfCG fUAG AAA AGfC AfUG fUfCA AAfG fCfCG GAA fCfCG fUfCfC-3' (ALT102128.01) (SEQ ID NO: 72). SPR data is provided herein which demonstrates that this aptamer bound to the EGFR recombinant protein (see FIG. 11, highest trace).

In an alternative or additional embodiment the 2'-F substitution is present at nucleotide position 39 and comprises the following sequence:
5'-GGA fCGG AfUfU fUAA fUfCG fCfCG fUAG AAA AGfC AfUG fUfCA AAG fCfCfG GAA fCfCG fUfCfC-3' (ALT102129.01) (SEQ ID NO: 73). SPR data is provided herein which demonstrates that this aptamer bound to the EGFR recombinant protein (see FIG. 11, third trace from top).

Figure 12:
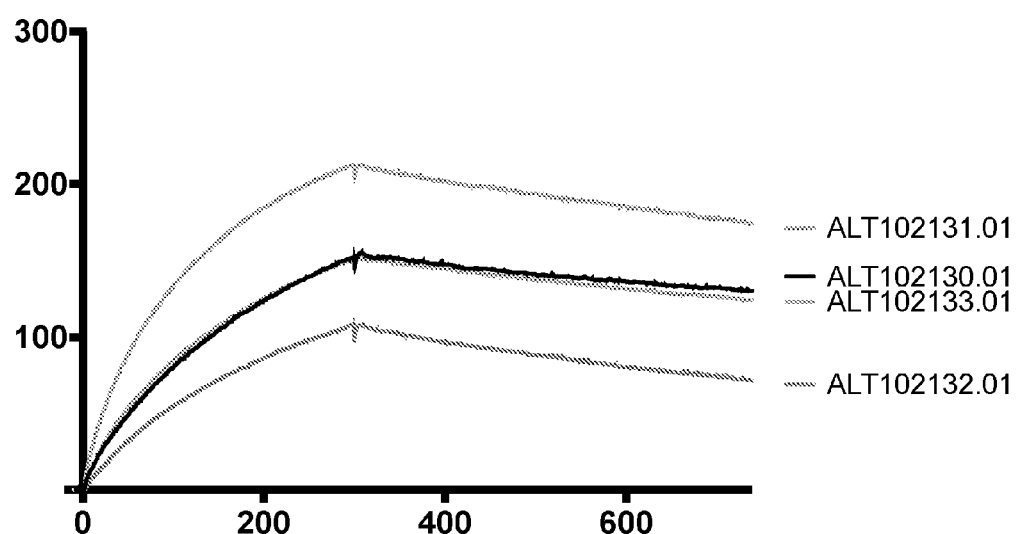

In an alternative or additional embodiment the 2'-F substitution is present at nucleotide position 40 and comprises the following sequence:
5'-GGA fCGG AfUfU fUAA fUfCG fCfCG fUAG AAA AGfC AfUG fUfCA AAG fCfCG fGAA fCfCG fUfCfC-3' (ALT102130.01) (SEQ ID NO: 74). SPR data is provided herein which demonstrates that this aptamer bound to the EGFR recombinant protein (see FIG. 12, second trace from top).

In an alternative or additional embodiment the 2'-F substitution is present at nucleotide position 41 and comprises the following sequence:
5'-GGA fCGG AfUfU fUAA fUfCG fCfCG fUAG AAA AGfC AfUG fUfCA AAG fCfCG GfAA fCfCG fUfCfC-3' (ALT102131.01) (SEQ ID NO: 75). SPR data is provided herein which demonstrates that this aptamer bound to the EGFR recombinant protein (see FIG. 12, highest trace).

In an alternative or additional embodiment the 2'-F substitution is present at nucleotide position 42 and comprises the following sequence:
5'-GGA fCGG AfUfU fUAA fUfCG fCfCG fUAG AAA AGfC AfUG fUfCA AAG fCfCG GAfA fCfCG fUfCfC-3' (ALT102132.01) (SEQ ID NO: 76). SPR data is provided herein which demonstrates that this aptamer exhibited medium binding (i.e. a faster "off" or disassociation) to the EGFR recombinant protein (see FIG. 12, lowest trace).

In an alternative or additional embodiment the 2'-F substitution is present at nucleotide position 45 and comprises the following sequence:
5'-GGA fCGG AfUfU fUAA fUfCG fCfCG fUAG AAA AGfC AfUG fUfCA AAG fCfCG GAA fCfCfG fUfCfC-3' (ALT102133.01) (SEQ ID NO: 77). SPR data is provided herein which demonstrates that this aptamer bound to the EGFR recombinant protein (see FIG. 12, third trace from top).

In a further embodiment, the 2'-F substitution is present at one or more or even each of positions 2 to 3, 5 to 7, 11, 15, 20 to 26, 28, 33, 36, 39 to 41 and 45 (i.e. the sequences set out hereinbefore). These positions provide the advantage of demonstrating a good level of binding to the EGFR recombinant protein from the SPR data provided herein.

It will be appreciated that any of the aforementioned embodiments of the 2'-OMe substitutions may be combined with any of the aforementioned embodiments of the 2'-F substitutions. For example, in one embodiment, the 2'-OMe substitution is present at one or more or even each of positions 1 to 3, 5 to 7, 15, 18, 20 to 21, 23 to 24, 26, 28, 30, 33, 36, 39 to 41 and 45 (i.e. the sequences set out hereinbefore) and the 2'-F substitution is present at one or more or even both of the A and G nucleotides at positions 11 and 25 and each of the 2'-OH groups of the C and U nucleotides are modified to a 2'-F group. In a further embodiment, the 2'-OMe substitution is present at each of positions 1 to 3, 5 to 7, 15, 18, 20 to 21, 23 to 24, 26, 28, 30, 33, 36, 39 to 41 and 45 and the 2'-F substitution is present at both positions 11 and 25 and each of the 2'-OH groups of the C and U nucleotides are modified to a 2'-F group, for example:
5'-mGmGmA fCmGmG mAfUfU fUfAA fUfCmG fCfCmG fUmAmG AmAmA fAmGfC mAfUmG fUfCmA AAmG fCfCmG mGmAA fCfCmG fUfCfC-3' (ALT102137.01) (SEQ ID NO: 78). The aptamer of this embodiment exhibited a good level of binding to the EGFR recombinant protein from the SPR data provided herein (see FIG. 14, sixth trace from top).

It will also be appreciated that any of the aforementioned embodiments of the 2'-OMe substitutions may be combined with any of the aforementioned absences of $X_1$-$X_9$ and $X_{45}$-$X_{47}$. For example, in one embodiment, $X_3$-$X_5$ and $X_{45}$-$X_{47}$ are absent, $X_1$, $X_2$ and $X_6$ are G, $X_7$ is A, $X_8$ and $X_9$ are U, the 2'-OMe substitution is present at one or more or even each of positions 1 to 2, 6 to 7, 15, 18, 20 to 21, 23 to 24, 26, 28, 30, 33, 36 and 39 to 41 (i.e. the sequences set out hereinbefore with numbering being based on absent nucleotides being counted as present) and each of the 2'-OH groups of the C and U nucleotides are modified to a 2'-F group. In a further, $X_3$-$X_5$ and $X_{45}$-$X_{47}$ are absent, $X_1$, $X_2$ and $X_6$ are G, $X_7$ is A, $X_8$ and $X_9$ are fU, the 2'-OMe substitution is present at each of positions 1 to 2, 6 to 7, 15, 18, 20 to 21, 23 to 24, 26, 28, 30, 33, 36 and 39 to 41 (i.e. the sequences set out hereinbefore with numbering being based on absent nucleotides being counted as present) and each of the 2'-OH groups of the C and U nucleotides are modified to a 2'-F group, for example:
5'-mGmG mG mAfUfU fUAA fUfCmG fCfCmG fUmAmG AmAmA AmGfC mAfUmG fUfCmA AAmG fCfCmG mGmAA fCfCfC-3' (ALT102139.01) (SEQ ID NO: 79). The aptamer of this embodiment exhibited a medium level of binding (i.e. lower Rmax) to the EGFR recombinant protein from the SPR data provided herein (see FIG. 15, fourth trace from top) and a good level of binding to two EGFR cell types from the FACS data provided herein (see FIG. 18 for binding to LN-18 cells and FIG. 19 for binding to A549 cells).

It will also be appreciated that any of the aforementioned embodiments of the 2'-OMe substitutions may be combined with any of the aforementioned absences of $X_1$-$X_9$ and $X_{45}$-$X_{47}$ and any of the aforementioned embodiments of the 2'-OMe substitutions. For example, in one embodiment, $X_3$-$X_5$ and $X_{45}$-$X_{47}$ are absent, $X_1$, $X_2$ and $X_6$ are G, $X_7$ is A, $X_8$ and $X_9$ are U, the 2'-OMe substitution is present at one or more or even each of positions 1 to 2, 6 to 7, 15, 18, 20 to 21, 23 to 24, 26, 28, 30, 33, 36 and 39 to 41 (i.e. the sequences set out hereinbefore with numbering being based on absent nucleotides being counted as present) and the 2'-F substitution is present at one or more or even both of the A and G nucleotides at positions 11 and 25, and each of the 2'-OH groups of the C and U nucleotides are modified to a 2'-F group. In a further embodiment, $X_3$-$X_5$ and $X_{45}$-$X_{47}$ are absent, $X_1$, $X_2$ and $X_6$ are G, $X_7$ is A, $X_8$ and $X_9$ are fU, the 2'-OMe substitution is present at each of positions 1 to 2, 6 to 7, 15, 18, 20 to 21, 23 to 24, 26, 28, 30, 33, 36 and 39 to 41 (i.e. the sequences set out hereinbefore with numbering being based on absent nucleotides being counted as present), and the 2'-F substitution is present at one or more or even both of the A and G nucleotides at positions 11 and 25, and each of the 2'-OH groups of the C and U nucleotides are modified to a 2'-F group, for example:
5'-mGmG mG mAfUfU fUfAA fUfCmG fCfCmG fUmAmG AmAmA fAmGfC mAfUmG fUfCmA AAmG fCfCmG mGmAA fCfCfC-3' (ALT102140.01) (SEQ ID NO: 80). The aptamer of this embodiment exhibited a medium level of binding (i.e. lower Rmax) to the EGFR recombinant protein from the SPR data provided herein (see FIG. 15, second trace from top).

Figure 17:
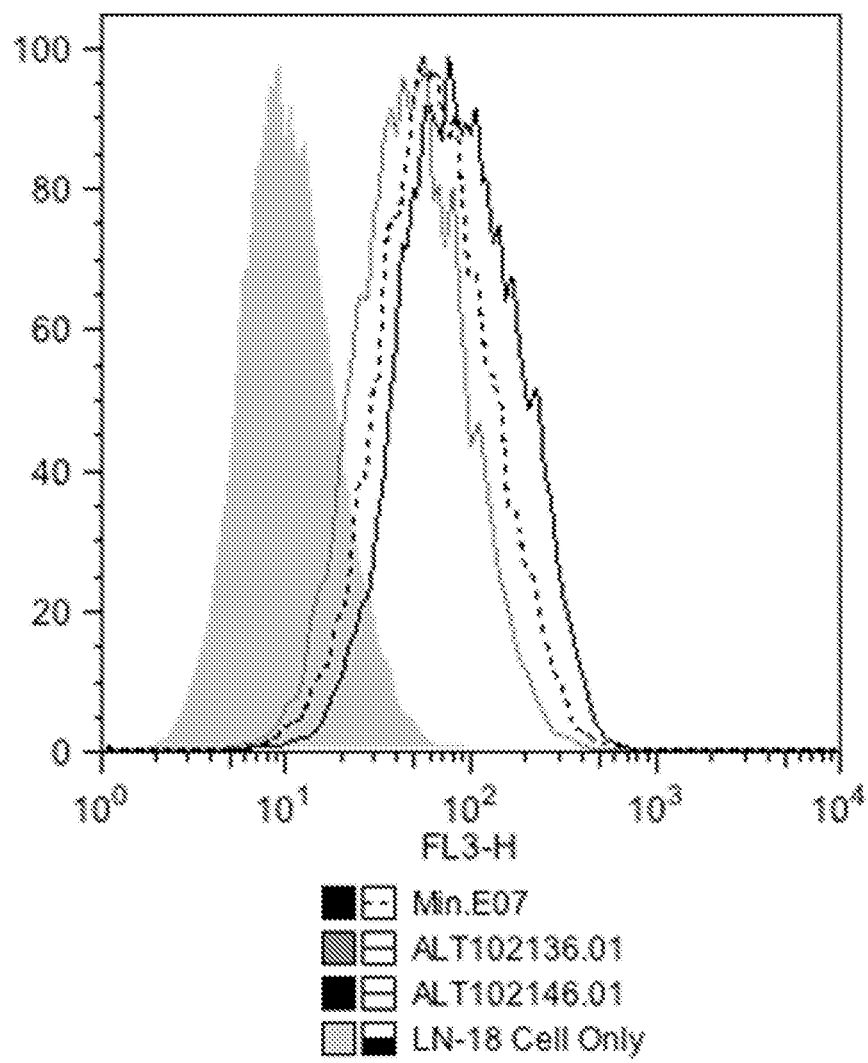

In one embodiment, the nucleotide molecule additionally comprises one or more further modifications, such as a 3' capping modification. In one embodiment, the 3' capping modification comprises the addition of an inverted thymidine nucleotide (i-dT) at the 3' end of said ribonucleic acid molecule. The 3'-3' phosphate connection is not readily recognized by nucleases and thereby reduces the exonuclease activity from the 3'-end of the oligonucleotide conferring additional nuclease stability. This is fully described in L Beigelman et al (1995) J. Biol. Chem, 270, 25702-25708. In one embodiment, the i-dT modification is added to the 3' end of ALT102135.01 (i.e. SEQ ID NO: 51). The aptamer of this embodiment (ALT102136.01) not only conferred nuclease stability upon the resultant ribonucleic acid molecule as shown in the serum degradation data provided herein (see FIGS. 20-22) but surprisingly also retained both a good level of binding to the EGFR recombinant protein from the SPR data provided herein (see FIG. 14, fourth trace from top) and a good level of binding to EGFR cells from the FACS data provided herein (see FIG. 17 for binding to LN-18 cells).

In an alternative embodiment, the i-dT modification is added to the 3' end of ALT102137.01 (i.e. SEQ ID NO: 78). The aptamer of this embodiment (ALT102138.01) not only conferred nuclease stability upon the resultant ribonucleic acid molecule as shown in the serum degradation data provided herein (see FIGS. 20-22) but surprisingly also retained a good level of binding to the EGFR recombinant protein from the SPR data provided herein (see FIG. 14, eighth trace from top).

The skilled person will be aware that nucleotide sequences with greater than 48 nucleotides (but no more than 63 nucleotides, i.e. the 48 maximum nucleotides of SEQ ID NO: 1 plus no more than 15 additional nucleotides) are also within the scope of the invention. Thus, in one embodiment the ribonucleic acid molecule comprises additional nucleotides at the 5' or 3' end. It will be appreciated that any number of nucleotides may be added at the 5' or 3' end, typically between 1 and 15 nucleotides, such as between 1 and 10 nucleotides, in particular between 1 and 5 nucleotides, more particularly between 2 and 4 nucleotides, for example 3 or 4 nucleotides. In one embodiment, the nucleotides are added at the 5' end. In a further embodiment, the added nucleotides comprise an AAA or AAAG nucleotide motif. Thus, in a yet further embodiment the ribonucleic acid molecule comprises a nucleotide sequence selected from: 5'-AAAX$_1$X$_2$X$_3$ X$_4$X$_5$X$_6$ X$_7$X$_8$X$_9$ U$_{10}$A$_{11}$A$_{12}$ $U_{13}C_{14}G_{15}$ $G_{16}G_{17}G_{18}$ $U_{19}A_{20}G_{21}$ $A_{22}A_{23}A_{24}$ $A_{25}G_{26}C_{27}$ $A_{28}U_{29}G_{30}$ $U_{31}C_{32}A_{33}$ $A_{34}A_{35}G_{36}$ $C_{37}C_{38}G_{39}$ $G_{40}A_{41}A_{42}$ $C_{43}C_{44}X_{45}X_{46}X_{47}C_{48}$-3' (SEQ ID NO: 81) or
5'-AAAG$X_1X_2X_3$ $X_4X_5X_6$ $X_7X_8X_9$ $U_{10}A_{11}A_{12}$ $U_{13}C_{14}G_{15}$ $G_{16}C_{17}G_{18}$ $U_{19}A_{20}G_{21}$ $A_{22}A_{23}A_{24}$ $A_{25}G_{26}C_{27}$ $A_{28}U_{29}G_{30}$ $U_{31}C_{32}A_{33}$ $A_{34}A_{35}G_{36}$ $C_{37}C_{38}G_{39}$ $G_{40}A_{41}A_{42}$ $G_{43}C_{44}X_{45}$ $X_{46}X_{47}C_{48}$-3' (SEQ ID NO: 82), wherein $X_1$-$X_9$ and $X_{45}$-$X_{47}$ are as defined hereinbefore.

It will also be appreciated that any or all of the aforementioned additional nucleotides may contain a 2'-OMe substitution. For example, in the embodiment where $X_1$-$X_9$ and $X_{45}$-$X_{47}$ are present and each of the 2'-OH groups of the C and U nucleotides are modified to a 2'-F group and the nucleotide sequence comprises an AAA motif as additional nucleotides at the 5' end, all of said additional nucleotides may contain a 2'-OMe substitution. Thus, in one embodiment the ribonucleic acid molecule comprises a nucleotide sequence selected from:
5'-mAmAmA GGA fCGG AfUfU fUAA fUfCG fCfCG fUAG AAA AGfC AfUG fUfCA AAG fCfCG GAA fCfCG fUfCfC-3' (ALT102145.01) (SEQ ID NO: 83). This aptamer demonstrated a good level of binding to the EGFR recombinant protein from the SPR data provided herein (see FIG. 14, highest trace) and a good level of binding to two EGFR cell types from the FACS data provided herein (see FIG. 18 for binding to LN-18 cells and FIG. 19 for binding to A549 cells).

In an alternative example, $X_1$-$X_4$ and $X_{45}$-$X_{47}$ are absent, $X_5$-$X_9$ are present and each of the 2'-OH groups of the C and U nucleotides are modified to a 2'-F group and the nucleotide sequence comprises an AAAG motif as additional nucleotides at the 5' end, all of said additional nucleotides may contain a 2'-OMe substitution and additional 2'-OMe substitutions may be present at each of positions 5 to 7, 15, 18, 20 to 21, 23 to 24, 26, 28, 30, 33, 36 and 39 to 41 (with numbering being based on absent nucleotides being counted as present). Thus, in one embodiment the ribonucleic acid molecule comprises a nucleotide sequence selected from:
5'-mAmAmAmG mGmG mAfUfU fUAA fUfCmG fCfCmG fUmAmG AmAmA AmGfC mAfUmG fUfCmA AAmG fCfCmG mGmAA fCfCfC-3' (ALT102146.01) (SEQ ID NO: 84). This aptamer demonstrated a good level of binding to the EGFR recombinant protein from the SPR data provided herein (see FIG. 15, third trace from top) and a good level of binding to EGFR cells from the FACS data provided herein (see FIG. 17 for binding to LN-18 cells).

In one particular embodiment which may be mentioned, the ribonucleic acid molecule comprises a nucleotide sequence selected from:

(ALT102054.01)
(SEQ ID NO: 6)
5'-GGG AfUfU fUAA fUfCG fCfCG fUAG AAA AGfC AfUG fUfCA AAG fCfCG GAA fCfCfC-3';

(ALT102066.01)
(SEQ ID NO: 18)
5'-GGA fCGG AfUmU fUAA fUfCG fCfCG fUAG AAA AGfC AfUG fUfCA AAG fCfCG GAA fCfCG fUfCfC-3';

(ALT102067.01)
(SEQ ID NO: 19)
5'-GGA fCGG AfUfU mUAA fUfCG fCfCG fUAG AAA AGfC AfUG fUfCA AAG fCfCG GAA fCfCG fUfCfC-3';

(ALT102068.01)
(SEQ ID NO: 20)
5'-GGA fCGG AfUfU fUmAA fUfCG fCfCG fUAG AAA AGfC AfUG fUfCA AAG fCfCG GAA fCfCG fUfCfC-3';

(ALT102135.01)
(SEQ ID NO: 51)
5'-mGmGmA fCmGmG mAfUfU fUAA fUfCmG fCfCmG fUmAmG AmAmA AmGfC mAfUmG fUfCmA AAmG fCfCmG mGmAA fCfCmG fUfCfC-3';

(ALT102136.01)
5'-mGmGmA fCmGmG mAfUfU fUAA fUfCmG fCfCmG fUmAmG AmAmA AmGfC mAfUmG fUfCmA AAmG fCfCmG mGmAA fCfCmG fUfCfC-3'i-dT;

(ALT102139.01)
(SEQ ID NO: 79)
5'-mGmG mG mAfUfU fUAA fUfCmG fCfCmG fUmAmG AmAmA AmGfC mAfUmG fUfCmA AAmG fCfCmG mGmAA fCfCfC-3';

(ALT102145.01)
(SEQ ID NO: 83)
5'-mAmAmA GGA fCGG AfUfU fUAA fUfCG fCfCG fUAG AAA AGfC AfUG fUfCA AAG fCfCG GAA fCfCG fUfCfC-3';
and (ALT102146.01)
(SEQ ID NO: 84)
5'-mAmAmAmG mGmG mAfUfU fUAA fUfCmG fCfCmG fUmAmG AmAmA AmGfC mAfUmG fUfCmA AAmG fCfCmG mGmAA fCfCfC-3'.

The aptamers of this embodiment of the invention provided the advantage of not only demonstrating binding to recombinant EGFR protein but also binding to at least one type of EGFR cells.

In one particular embodiment which may be mentioned, the ribonucleic acid molecule comprises a nucleotide sequence selected from:

(ALT102054.01)
(SEQ ID NO: 6)
5'-GGG AfUfU fUAA fUfCG fCfCG fUAG AAA AGfC AfUG fUfCA AAG fCfCG GAA fCfCfC-3';

(ALT102135.01)
(SEQ ID NO: 51)
5'-mGmGmA fCmGmG mAfUfU fUAA fUfCmG fCfCmG fUmAmG AmAmA AmGfC mAfUmG fUfCmA AAmG fCfCmG mGmAA fCfCmG fUfCfC-3';

(ALT102139.01)
(SEQ ID NO: 79)
5'-mGmG mG mAfUfU fUAA fUfCmG fCfCmG fUmAmG AmAmA AmGfC mAfUmG fUfCmA AAmG fCfCmG mGmAA fCfCfC-3';
and (ALT102145.01)
(SEQ ID NO: 83)
5'-mAmAmA GGA fCGG AfUfU fUAA fUfCG fCfCG fUAG AAA AGfC AfUG fUfCA AAG fCfCG fUfCfC-3'.

The aptamers of this embodiment of the invention provided the advantage of not only demonstrating binding to recombinant EGFR protein but also binding to two types of EGFR cells (i.e. A431 and A549 or LN-18 and A549).

Aptamer Synthesis

It will be apparent to the skilled person that the aptamers of the invention may be synthesised in accordance with techniques within the common general knowledge, such as solid phase nucleotide synthesis (C R Noe, L Kaufhold; Chemistry of Antisense Oligonucleotides in New Trends in Synthetic Medicinal Chemistry, Ed: F Gualtieri; Wiley-VCH, Weinheim, 2000; pp 261-347. ISBN 3527297995).

Cancer Cell Binding Complexes

As discussed hereinbefore, the aptamers of the invention provide a promising target for the treatment of cancer by combining them with immune response generating moieties (as set out in WO 2005/079423). Thus, according to a further aspect of the invention, there is provided a cancer cell binding complex which comprises an aptamer as defined herein conjugated, or otherwise linked, to an immunogenic molecule. The aptamers of the invention provide the advantage of imparting effective binding between the cancer cell binding complex and cancer cell. Synergistically, the presence of the immunogenic molecule in the complex provides a means for the immune system of the individual to specifically and selectively target and destroy cancer cells without the bystander effect which is seen in many anti-cancer therapies where normal, healthy cells are destroyed.

Examples of immunogenic molecules include moieties capable of binding to an immune response component of an individual. In one embodiment, the immunogenic molecule is selected from: the alpha-Gal epitope (i.e. galactosyl-alpha-1,3-galactosyl-beta-1,4-N-acetylglucosamine), dinitrophenyl (DNP) and L-rhamnose. In a yet further embodiment, the immunogenic molecule is the alpha-Gal epitope (i.e. galactosyl-alpha-1,3-galactosyl-beta-1,4-N-acetylglucosamine).

In one embodiment, a spacer is present between the aptamer and the immunogenic molecule. The spacer provides the advantage of allowing sufficient flexibility and steric positioning of the complex when bound to the cancer cell to allow recognition and binding of the immune response component to the immunogenic molecule. In one embodiment, the spacer comprises a plurality of carbon residues, such as greater than 5, in particular 9 carbon residues. In an alternative embodiment, the spacer comprises one or more polyether groups, such as polyethylene glycol.

Pharmaceutical Compositions

While it is possible for the cancer cell binding complex to be administered alone, it is preferable to present it as a pharmaceutical composition (e.g. formulation).

Thus, according to a further aspect, the invention provides a pharmaceutical composition, and methods of making a pharmaceutical composition comprising (e.g admixing) at least one cancer cell binding complex, together with one or more pharmaceutically acceptable excipients and optionally other therapeutic or prophylactic agents, as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity (i.e. generally recognised as safe (GRAS)), irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing cancer cell binding complexes can be formulated in accordance with known techniques, see for example, Remington's Pharmaceutical Sciences, Mack Publishing Company, Easton, Pa., USA.

The pharmaceutical compositions can be in any form suitable for parenteral, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use.

The pharmaceutical formulation can be prepared by lyophilising a cancer cell binding complex. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use.

Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening or coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for sub-cutaneous (s.c.) administration.

The cancer cell binding complex may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical compositions typically comprise from approximately 1% (w/w) to approximately 95% (w/w) active ingredient and from 99% (w/w) to 5% (w/w) of a pharmaceutically acceptable excipient or combination of excipients. Preferably, the compositions comprise from approximately 20% (w/w) to approximately 90% (w/w) active ingredient and from 80% (w/w) to 10% of a pharmaceutically acceptable excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The cancer cell binding complex will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

The active compound will be administered to a patient in need thereof (for example a human or animal patient) in an amount sufficient to achieve the desired therapeutic effect.

Anti-Cancer Therapy

According to a further aspect of the invention, there is provided a cancer cell binding complex as defined herein for use in the treatment of cancer.

According to a further aspect of the invention, there is provided the use of a cancer cell binding complex as defined herein in the manufacture of a medicament for use in the treatment of cancer.

According to a further aspect of the invention, there is provided a method of treating cancer which comprises administering to an individual in need thereof a cell binding complex as defined herein.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenous leukemia [AML], chronic myelogenous leukemia [CML], chronic myelomonocytic leukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocytic leukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcoma protuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wlms tumour, and primitive neuroectodermal tumours); or syndromes, congenital or otherwise, which leave the patient susceptible to malignancy (for example Xeroderma Pigmentosum).

In one embodiment, the cancer the cancer is selected from lung and colorectal cancer.

The complexes are generally administered to a subject in need of such administration, for example a human or animal patient, preferably a human.

The cancer cell binding complexes will typically be administered in amounts that are therapeutically or prophylactically useful and which generally are non-toxic. However, in certain situations (for example in the case of life threatening diseases), the benefits of administering a cancer cell binding complex may outweigh the disadvantages of any toxic effects or side effects, in which case it may be considered desirable to administer cancer cell binding complexes in amounts that are associated with a degree of toxicity.

The cancer cell binding complexes may be administered over a prolonged term to maintain beneficial therapeutic effects or may be administered for a short period only. Alternatively they may be administered in a continuous manner or in a manner that provides intermittent dosing (e.g. a pulsatile manner).

A typical daily dose of the cancer cell binding complex can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The cancer cell binding complex can be administered on a daily basis or on a repeat basis every 2, or 3, or 4, or 5, or 6, or 7, or 10 or 14, or 21, or 28 days for example.

The cancer cell binding complex may be administered in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The cancer cell binding complex may be administered once or more than once each day. The cancer cell binding complex can be administered continuously (i.e. taken every day without a break for the duration of the treatment regimen). Alternatively, the cancer cell binding complex can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a cancer cell binding complex for periods of one hour daily for up to ten days in particular up to five days for one week, and the treatment repeated at a desired interval such as two to four weeks, in particular every three weeks.

More particularly, a patient may be given an infusion of a compound of the formula (I) for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of cancer cell binding complex administered and the type of composition used will be commensurate with the nature of the disease or physiological condition being treated and will be at the discretion of the physician.

It will be appreciated that cancer cell binding complexes can be used as a single agent or in combination with other anticancer agents. Combination experiments can be performed, for example, as described in Chou T C, Talalay P. Quantitative analysis of dose-effect relationships: the combined effects of multiple drugs or enzyme inhibitors. Adv Enzyme Regulat 1984; 22: 27-55.

Examples of other therapeutic agents or treatments that may be administered together (whether concurrently or at different time intervals) with the cancer cell binding complexes include but are not limited to:

Topoisomerase I inhibitors;
Antimetabolites;
Tubulin targeting agents;
DNA binder and topoisomerase II inhibitors;
Alkylating Agents;
Monoclonal Antibodies;
Anti-Hormones;
Signal Transduction Inhibitors;
Proteasome Inhibitors;
DNA methyl transferases;
Cytokines and retinoids;
Chromatin targeted therapies;
Radiotherapy; and
Other therapeutic or prophylactic agents.

Where the cancer cell binding complex is administered in combination therapy with one, two, three, four or more other therapeutic agents (preferably one or two, more preferably one), the agents can be administered simultaneously or sequentially. In the latter case, the two or more agents will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

It will be appreciated that the preferred method and order of administration and the respective dosage amounts and regimes for each component of the combination will depend on the particular other medicinal agent and cancer cell binding complex of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the cancer cell binding complex according to the present invention and the one or more other anticancer agent(s) when given as a combination may be determined by the person skilled in the art. Said ratio and the exact dosage and frequency of administration depends on the particular cancer cell binding complex according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the cancer cell binding complexes of the present invention. A particular weight ratio for the present cancer cell binding complex and another anticancer agent may range from 1/10 to 10/1, more in particular from 1/5 to 5/1, even more in particular from 1/3 to 3/1.

The cancer cell binding complexes of the invention may also be administered in conjunction with non-chemotherapeutic treatments such as radiotherapy, photodynamic therapy, gene therapy; surgery and controlled diets.

For use in combination therapy with another chemotherapeutic agent, the cancer cell binding complex and one, two, three, four or more other therapeutic agents can be, for example, formulated together in a dosage form containing two, three, four or more therapeutic agents i.e. in a unitary pharmaceutical composition containing all components. In an alternative embodiment, the individual therapeutic agents may be formulated separately and presented together in the form of a kit, optionally with instructions for their use.

The following studies illustrate the utility of aptamers of the invention:

EXAMPLE 1

Binding Analysis to EGFR Recombinant Protein Using Surface Plasmon Resonance (SPR)

Aptamer binding to EGFR recombinant protein was assessed by surface plasmon resonance (SPR). SPR experiments were performed on a 404pi system (BiOptix, Boulder, Colo.), at a constant temperature of 20° C., 20 µL min$^{-1}$ flow rate, using running buffer (degassed PBS, 5 mM $MgCl_2$, 0.05% Tween) for all coupling and capture steps. 0.1 M N-hydroxysuccinimide (NHS) in MOPS, 0.4 M 1-ethyl-3-(3-dimethylaminopropyl) carbodiimide hydrochloride (EDC), 1 M ethanolamine hydrochloride (pH 8.5) and 10 mM sodium acetate pH 4.5, were from Sigma (St. Louis, Mo.). EGFR was obtained from R&D Systems (Minneapolis, Minn.). Three 96 well plates of oligonucleotides were synthesized by solid phase phosphoramidite chemistry by Boston Open Labs (Cambridge, Mass.) with a 5' biotin.

The surface in all four channels of a CDM150 sensor chip (BiOptix) was activated by injecting 140 µL of a 1:1 mixture (v/v) of EDC and NHS. Then 350 µL of 285 nM EGFR in 10 mM sodium acetate pH 4.5 was injected in all 4 channels and covalently bound to a density of ~8000 Response Units (RU) over 1050 sec. Finally, the surface was blocked by an injection of 200 µL 1 M ethanolamine hydrochloride.

Aptamer binding kinetics were measured by injection over the functionalized chip. Aptamers were diluted to between 50 and 250 nM, and each was screened in 100 µL injection, followed by a dissociation phase of 400 sec. In lieu of a reference channel, buffer injections were utilized in between 2-3 sets of aptamers for background subtraction. Data was processed and analyzed using Scrubber (BioLogic Software, Campbell, Australia).

Alternatively, an Octet Red 96 (ForteBio, Menlo Park, Calif.) was utilized for aptamer sets starting with ALT102134.01. Sample buffer containing DPBS (no Mg, no Ca) was supplemented with 5 mM $MgCl_2$ and 0.05% tween-20 and used for dilutions, baseline and dissociation steps. For these assays, streptavidin pins were functionalized with 100 nM biotinylated aptamer solutions for 400 sec. Association was measured with 50 nM EGFR in sample buffer for 400 sec. Dissociation was measured in sample buffer. Data was processed and analyzed using ForteBio Data Analysis software.

The results of the SPR analysis are shown in FIGS. 1 to 15 wherein it can be seen that the majority of the tested aptamers demonstrated a good level of binding to the recombinant EGFR protein. In certain analyses, the known aptamer (MinE07) was also tested as a control and it can be seen that most aptamers of the invention either demonstrated equivalent or better binding to EGFR recombinant protein than MinE07.

EXAMPLE 2

Binding Analysis to EGFR Cells Using Flow Cytometry

Aptamer binding to EGFR expressing cells was assessed by flow cytometry (FCM). Prior to assay, biotinylated aptamers were thermally equilibrated at 65° C. for 5 mins followed by cooling at 0.1° C./sec to room temperature. Adherent cells were dissociated from flasks using non-enzymatic cell dissocation buffer (NECDB; Gibco, Carlsbad Calif.) and washed with DPBS (no Mg no Ca; Sigma).

In a typical assay 12-well cell culture plates were inoculated with cells (A431, LN-18, or MDA-MB-435) and grown to ~90% confluence over 1-2 days. Culture media was removed and cells were washed twice with at least 1 mL of binding buffer then blocked in 250 µL binding buffer binding buffer (DPBS containing 0.1 mg/ml tRNA) supplemented with 1 mg/ml BSA for 10 mins at room temperature. The supernatant was removed and cells were incubated in binding buffer containing 50 or 100 nM synthesized aptamer rocking at room temperature for 30 mins. Supernatant was removed and cells were washed three times with 500 µL wash buffer (DPBS containing 0.1 mg/mL tRNA). Cells were stained in 250 µL wash buffer supplemented with 0.5 µL Streptavidin PE-Cy 5.5 (SA-PE-Cy) or Streptavidin-Alexafluor 488 (SA-AF) (Invitrogen, Carlsbad, Calif.) and incubated for 10 minutes at room temperature. Cells were washed twice in 500 µL wash buffer and then dissociated from the culture plates with 250 µL NECDB. Free cells were transferred to 5 mL round bottom falcon tubes (BD Biosciences, San Jose, Calif.) and the plates were washed with 750 µL modified DPBS (with Mg and Ca; Sigma). Cells were collected by centrifugation, resuspended with 300 µL wash buffer. Cells were analyzed by flow cytometry on a FACSCalibur (BD Biosciences, San Jose, Calif.).

The results of the flow cytometry analysis are shown in FIGS. 16 to 19 wherein it can be seen that all tested aptamers demonstrated a good level of binding to EGFR cell types A431, LN-18 and/or A549 (the shaded trace to the left in each Figure represents the trace observed in the absence of aptamer). The known aptamer (MinE07) was also tested as a control and it can be seen that all tested aptamers demonstrated equivalent binding to EGFR cells. Furthermore, it can be seen that certain aptamers (i.e. ALT102054.01, ALT102135.01, ALT102139.01 and ALT102145.01) bound to more than one EGFR cell type (i.e. A431 and A549 for ALT102054.01 and LN-18 and A549 for ALT102135.01, ALT102139.01 and ALT102145.01).

EXAMPLE 3

Stability Analysis Using a Serum Degradation Assay

Aptamer degradation by serum nucleases was assessed by comparing intensity of agarose separated fragments of aptamers upon serum incubations (SDA). Aptamers were chemically synthesized with a 5' biotin and a 3' inverted dT (idT) by Boston Open Labs. Upon thermal equilibration, 7.5 µM aptamer was incubated in 70% Sprague Dawley rat serum (Innovative Research; Novi, Mich.) from 0 to 36 hours and 10 uL was separated on a 2% size select E-gel (Invitrogen). The gel was imaged by UV excitation and bands were quantitated with ImageJ. Intensity was subtracted from background and compared to the 0 time point.

Figure 20:
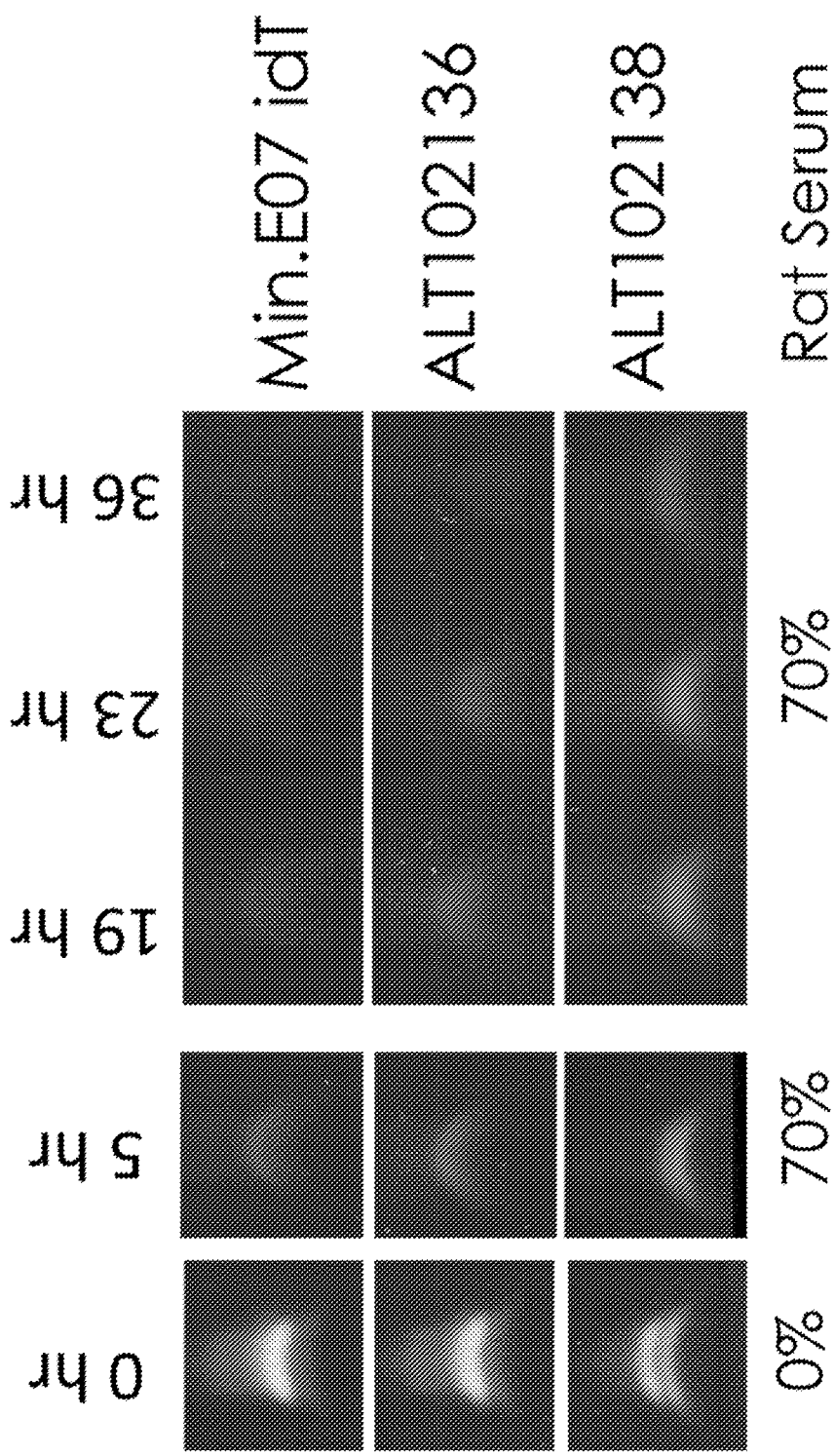
FIGS. 20 to 22 describe the results of the serum degradation assay analysis with 3' modified aptamers of the invention.
Figure 21:
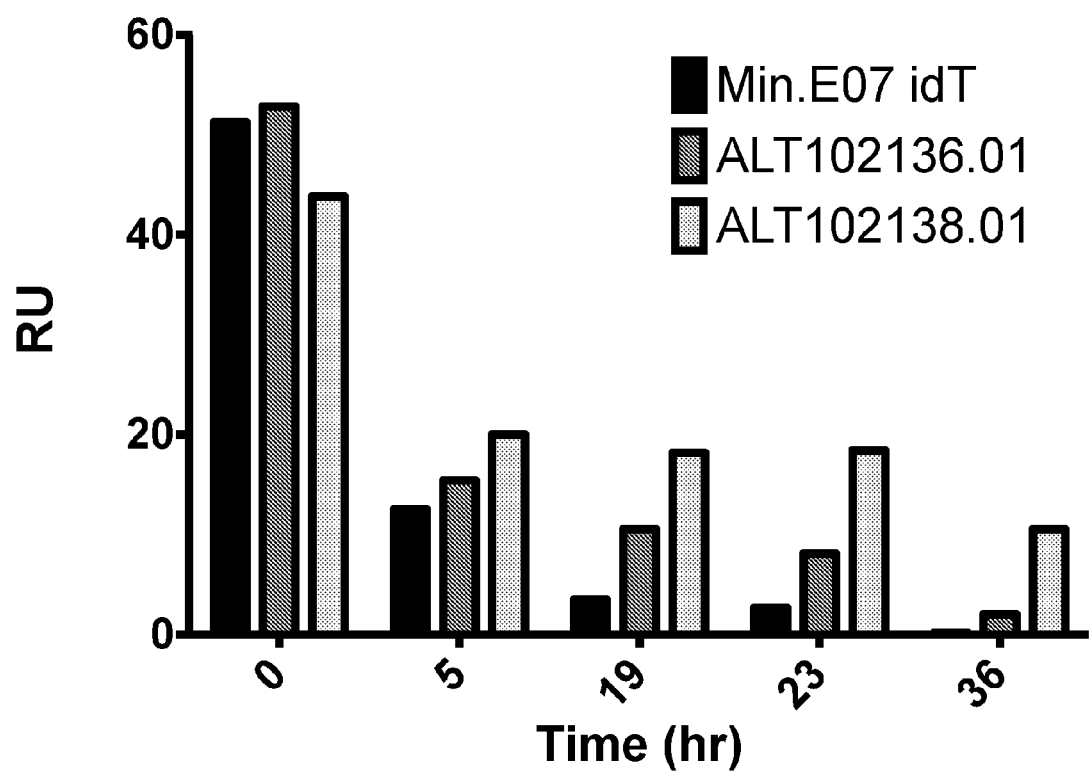
Figure 22:
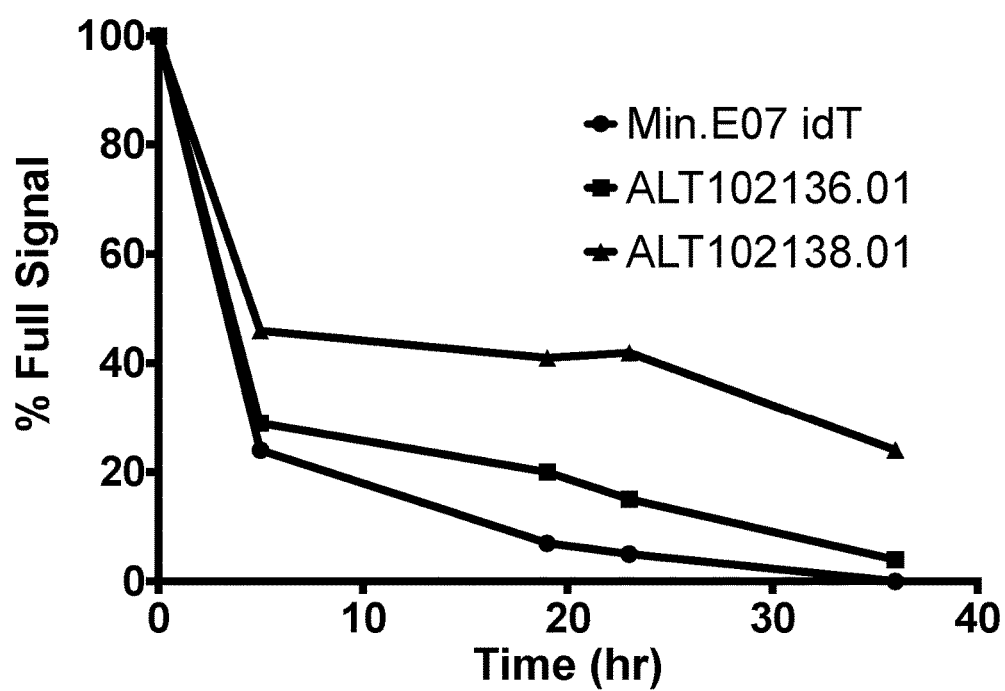

The results of the flow cytometry analysis are shown in FIGS. 20 to 22 wherein FIG. 20 presents the imaged gel, FIG. 21 presents a graph wherein the background has been subtracted from the signal and FIG. 22 presents a graph of % signal at the 0 hour timepoint with the background subtracted from the signal. It can be seen from the results in these Figures that both tested aptamers demonstrated a superior level of resistance against degradation when compared with the correspondingly modified known aptamer (MinE07 idT). The ALT102138 aptamer also appeared to demonstrate a greater level of resistance against degradation compared to ALT102136.

The invention claimed is:

1. A ribonucleic acid molecule comprising a nucleotide sequence:

5'-mGmG mG mAfUfU fUAA fUfCmG fCfCmG fUm-AmG AmAmA AmGfC mAfUmG fUfCmA AAmG fCfCmG mGmAA fCfCfC-3' (ALT102139.01) (SEQ ID NO: 79), wherein "m" represents a 2'-O-methyl substituted nucleotide and "f" represents a 2'-fluoro substituted nucleotide.

2. The ribonucleic acid molecule as defined in claim 1, which additionally comprises a 3' capping modification.

3. The ribonucleic acid molecule as defined in claim 2, which additionally comprises an addition of an inverted thymidine nucleotide (i-dT) at the 3' end of said ribonucleic acid molecule.

4. The ribonucleic acid molecule as defined in claim 1, wherein said one or more additional nucleotides comprise an additional AAA or AAAG nucleotide motif.

5. The ribonucleic acid molecule as defined in claim 4, wherein all of said additional nucleotides contain a 2'-OMe substitution.

6. The ribonucleic acid molecule as defined in claim 5, wherein said molecule has the sequence of:

(ALT102145.01)
(SEQ ID NO: 83)
5'-mAmAmA GGA fCGG AfUfU fUAA fUfCG fCfCG fUAG AAA AGfC AfUG fUfCA AAG fCfCG GAA fCfCG fUfCfC-3'.

7. The ribonucleic acid molecule as defined in claim 4, wherein all of said additional nucleotides contain a 2'-OMe substitution and said molecule has the sequence of:

(ALT102146.01)
(SEQ ID NO: 84)
5'-mAmAmAmG mGmG mAfUfU fUAA fUfCmG fCfCmG fUmAmG AmAmA AmGfC mAfUmG fUfCmA AAmG fCfCmG mGmAA fCfCfC-3'.

8. The ribonucleic acid molecule as defined in claim 4, wherein said one or more additional nucleotides comprise an additional AAA or AAAG nucleotide motif at the 5' end.

9. A cancer cell binding complex which comprises a ribonucleic acid molecule as defined in claim 1 conjugated to an immunogenic molecule.

10. The cancer cell binding complex as defined in claim 9, wherein the immunogenic molecule is selected from: the alpha-Gal epitope (i.e. galactosyl-alpha-1,3-galactosyl-beta-1,4-N-acetylglucosamine), dinitrophenyl (DNP) and L-rhamnose.

11. The cancer cell binding complex as defined in claim 9, wherein the immunogenic molecule is the alpha-Gal epitope (i.e. galactosyl-alpha-1,3-galactosyl-beta-1,4-N-acetylglucosamine).

12. A pharmaceutical composition comprising at least one cancer cell binding complex as defined in claim 9, together with one or more pharmaceutically acceptable excipients.

13. The pharmaceutical composition as defined in claim 12 further comprising other therapeutic or prophylactic agents.

14. A method for the treatment of cancer in a subject comprising:
administering a pharmaceutical composition comprising at least one cancer binding complex as defined in claim 9 to the subject.

* * * * *